United States Patent [19]
Ansari et al.

[11] Patent Number: 5,635,365
[45] Date of Patent: Jun. 3, 1997

[54] NONINVASIVE DIAGNOSIS FOR ALLOGRAFT REJECTION

[75] Inventors: Aftab A. Ansari, Stone Mountain; Francois Villinger, Decatur; Kenneth W. Sell, Atlanta, all of Ga.

[73] Assignee: Emory University, Atlanta, Ga.

[21] Appl. No.: 512,184

[22] Filed: Aug. 7, 1995

[51] Int. Cl.$^6$ .................................................. C12Q 1/48
[52] U.S. Cl. ................................................ 435/15; 435/30
[58] Field of Search ............................... 435/4, 15, 30, 435/184; 536/23.2

[56] References Cited

PUBLICATIONS

Shaked, A., The Role of Differential Class II Antigen Expression in Stimulation of Allogeneic Mixed Lymphocyte Reactions by Human Monocyte Hybridomas, Transplantation 53(6) 1341–1347 Jun. 1992.
Borresen, A., Screening for Base Mutations in the PAH and HPRT Loci Using the PCR in Combination with Denaturing Gradient Electrophoresis, Progress in Clinical and Biological Research 340A, Wiley–Liss, NY. 389–398 1990.
Albertini et al. (1982) Proc.Natl.Acad.Sci.USA 79:6617–6621. Genetics.
Nicklas et al. (1986) Mutation Research 173:67–72.
Ammenheuser et al. (1988) Mutation Research 204:509–520.
O'Neill et al. (1989) Environmental and Molecular Mitagemoso 13:289–293.
Edwards et al. (1990) Genomics 6:593–608.
Billingham (1990) Progress in Cardiovascular Diseases 33:11–18.
Kemkes, et al (1992) J. Heart Transplant 11:S221–S231.
Billingham et al. (1990) J. Heart Transplantation 9:587–593.
Miller et al. (1993) J. Am. Coll. Cardiol.22:41–54.
Ouwehand et al. (1993) Transplantation 56:1223–1229.
Jordan et al. (1993) Journal of Heart and Lung Transplantation 12:333–337.
Seshadri et al. (1983) Mutation Research 110:141–146.
Goulmy et al. (1989) Transplantation 48:559–563.
Albertini et al. (1985) Nature 316:369–371.
Allegretta et al. (1990) Science 247:718–721.
Sell et al. (1991) The Journal of Heart and Lung Transplantation 11:500–510.
Sala–Trepat et al. (1990) Mutagenesis 5:593–598.

*Primary Examiner*—Ralph Gitomer
*Attorney, Agent, or Firm*—Greenlee, Winner and Sullivan, P.C.

[57] ABSTRACT

The present invention provides a noninvasive method for diagnosing and/or predicting a rejection episode in a transplant patient, for example, in a heart transplant patient, by determining a rise in the frequency of thioguanine-resistant mutant peripheral blood mononuclear cells. Those resistant mutant cells have a deficiency in the purine salvage enzyme hypoxanthine guanine phosphoribosyltransferase. The relative frequency of the mutant cells in the population from a sample can be determined by direct plating in the presence of a selection medium and by determining of the mutation by polymerase chain reaction technology.

14 Claims, 13 Drawing Sheets

DAYS POST TRANSPLANTATION

↓ denotes day of histologically diagnosed rejection episode

DAYS POST TRANSPLANTATION

↓ denotes day of histologically diagnosed rejection episode

DAYS POST TRANSPLANTATION

↓ denotes day of histologically diagnosed rejection episode

↓ denotes day of histologically diagnosed rejection episode

DAYS POST TRANSPLANTATION

↓ denotes day of histologically diagnosed rejection episode

↓ denotes day of histologically diagnosed rejection episode

↓ denotes day of histologically diagnosed rejection episode

↓ denotes day of histologically diagnosed rejection episode

↓ denotes day of histologically diagnosed rejection episode

↓ denotes day of histologically diagnosed rejection episode

↓ denotes day of histologically diagnosed rejection episode

NONINVASIVE DIAGNOSIS FOR ALLOGRAFT REJECTION

This invention was made, at least in part, with funding from the National Institutes of Health. The United States Government may have certain rights in this invention.

FIELD OF THE INVENTION

The field of this invention is the area of allograft rejection and the diagnosis and/or prediction of allograft rejection. Specifically, the present invention provides a method for the diagnosis and/or prediction of immune rejection of transplanted organs or tissue, for example, a cardiac transplant; the rejection episode is diagnosed or predicted via determination of an increase in the frequency of peripheral blood mononuclear cells lacking hypoxanthine-guanine phosphoribosyltransferase activity.

BACKGROUND OF THE INVENTION

Nearly 2000 heart transplants are performed in the United States each year, and many other organs, such as lung, kidney, liver and pancreas, are transplanted into patients as well. There is a relatively stable population of about 16,000 to 20,000 heart transplant patients. Unfortunately, the average heart transplant patient survives only 8 to 10 years after receiving a transplant. New recipients, as well as the existing cohort of transplant recipients, need to be monitored for evidence of allograft rejection so that treatment can be administered as soon as possible. If transplant rejection is diagnosed relatively late, there is often significant tissue damage in the transplanted organ and hospitalization is almost inevitable. If the damage to the organ is extensive, a retransplant may also be required.

The current method for the monitoring and diagnosis of rejection after human cardiac transplant is invasive, and it entails the use of the transvenous myocardial bioptome to procure cardiac biopsy samples, which are then examined for histological evidence of rejection. A graded score of 0 to 4 is used; a score of 0 is assigned where there is no evidence of rejection and 4 is the maximum score of tissue damage and rejection. This pathology-graded score, together with clinical criteria, are used to institute immunosuppressive therapies for heart transplant patients with a diagnosis of rejection. By contrast, liver, kidney and lung transplants can be monitored by noninvasive enzymatic assays of urine and/or blood. However, in those cases, damage to the transplanted organ has occurred by the time diminished function is reflected in the tests, and the present invention provides an earlier method for diagnosis and/or prediction of rejection episodes.

The current method has certain other disadvantages in addition to being invasive. The greatest potential problem is sampling error due to the tendency of the bioptome to lodge in the same anatomic area of the heart. There is a small but real risk associated with the biopsy procedure, the procedure is costly, and there is a very high level of skill needed to perform the procedure.

Thus, there is a long-felt need in the art for a noninvasive, relatively inexpensive and accurate method for the assessment of the rejection state of a transplanted organ in a recipient patient.

SUMMARY OF THE INVENTION

The present invention provides a non-invasive method for the diagnosis and/or prediction of allograft rejection, for example, in human heart, lung, liver, kidney, bone marrow, pancreas or other solid organ transplant recipients. This method includes the step of obtaining a sample of blood, preferably peripheral blood, preferably with sequential samples, and determining the frequency of cells which undergo mutations in the gene encoding hypoxanthineguanine phosphoribosyltransferase (HPRT), comparing the frequency of said cells which have undergone mutations to the frequency of such mutations in the normal population, and diagnosing and/or predicting the occurrence of an allograft rejection where the frequency of Hprt-deficient cells of the transplant recipient exceeds the frequency in the normal population. One method of determining the frequency of Hprt-negative cells is selecting for the growth of those cells in the presence of 6-thioguanine and determining the FMC/$10^6$ (i.e., the frequency of Hprt-deficient cells per million cells). An alternative method for the detection of the number of cells undergoing mutation in the Hprt gene uses the polymerase chain reaction (PCR) technology in determining the frequency of Hprt$^-$ mutations in the transplant patient in comparison to the frequency in the normal population. Again, a rejection episode is predicted or diagnosed when the frequency in the transplant recipient increases beyond the frequency typical for the normal population or when, in sequential samples, a significant increase in the Hprt mutant frequency becomes evident. At that time, appropriate immunosuppressive therapy can be initiated in an attempt to protect the organ from immune destruction and preserve it in the patient in a functional state.

Also provided by the present invention is a method for diagnosing and/or predicting the incidence of a graft rejection episode, where the method includes the step of obtaining sequential PBMC samples, preferably at weekly intervals, and determining the frequency of Hprt$^-$ mutant cells in each sample. A graft rejection episode is diagnosed and/or predicted by an increase in the frequency of Hprt-deficient PBMCs and/or especially as compared with the frequency of such mutant cells in the normal population.

BRIEF DESCRIPTION OF THE FIGURES

FIG. 4B, Patient #14; FIG. 4C, Patient #15; FIG. 4D, Patient #16) showed a wide distribution of mutant cell frequencies, the data could be visualized only by using a log scale for the y-axis in these plots. In each case, the arrow is the time when rejection was diagnosed via a histological examination of endomyocardial biopsy tissue. Patient #13 died on day 276 after transplant, and at autopsy the graft failure was attributed to accelerated graft atherosclerosis.

FIG. 5B, Patient #18; FIG. 5C, Patient #19; FIG. 5D, Patient #20; FIG. 5E, Patient #21; FIG. 5F, Patient #22) are plotted on a linear scale on the y-axis. In each case, the arrow is the time when rejection was diagnosed via the histological examination of endomyocardial biopsy tissue.

DETAILED DESCRIPTION OF THE INVENTION

Figure 1:
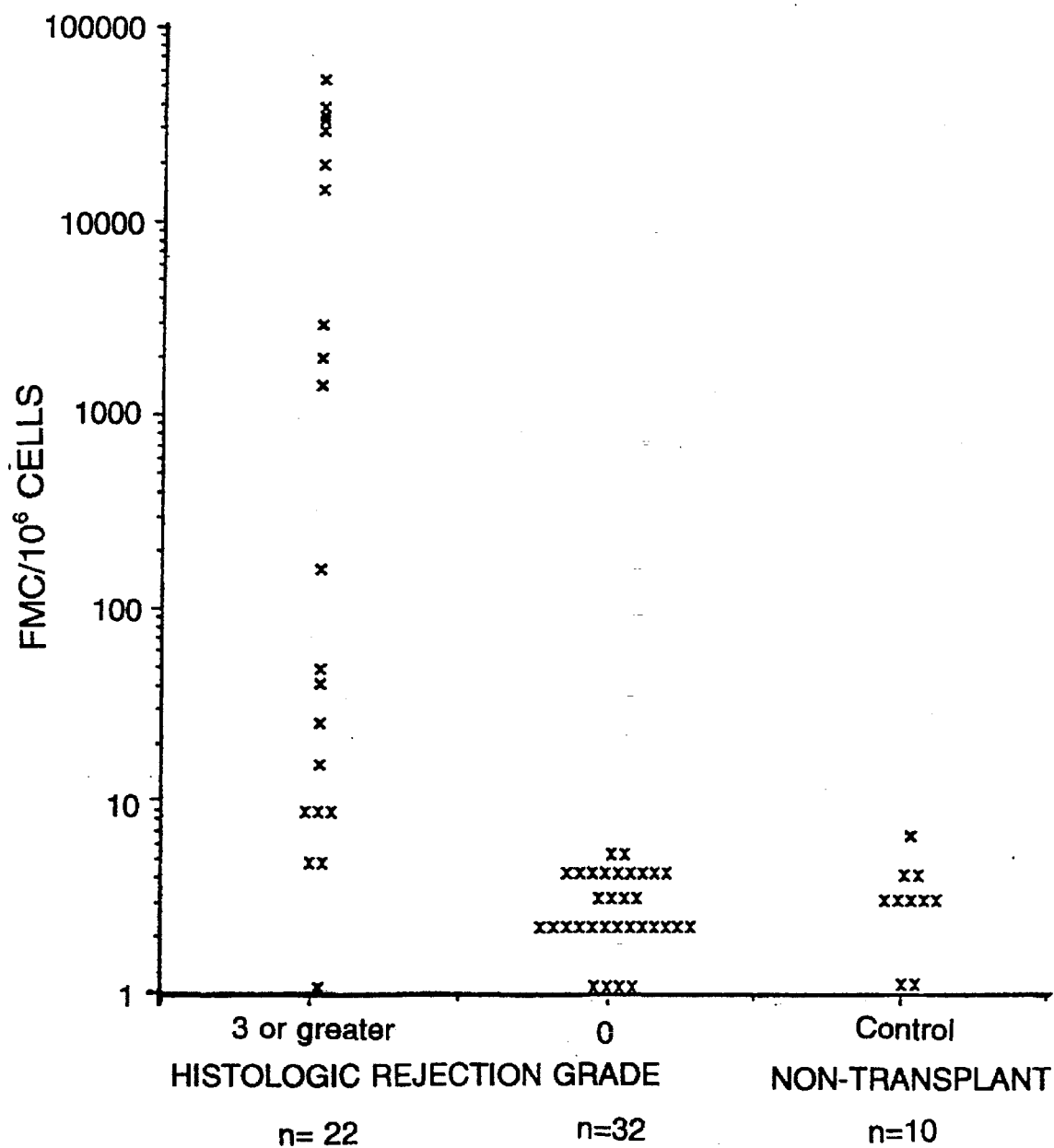
FIG. 1 graphically illustrates the results of the analyses of sequential peripheral blood mononuclear cells for the occurrence of Hprt-deficient mutant cells (FMC/$10^6$ cells) as described in Example 1. The control data represent the results for PBMC Hprt-deficient mutant analysis in 10 healthy human volunteers (laboratory personnel). The results for a series of 6–7 sequential PBMC samples for a total of 32 specimens obtained from 5 cardiac transplant patients with no history of rejection during this time series are presented in the position labeled 0 (Histological Rejection Grade). A series of 22 PBMC samples from transplant patients with a Histological Rejection Grade of 3 or greater (reflecting moderate to severe rejection) were also analyzed.

For many patients, an organ transplant is the only hope of survival. One of the relatively common complications after organ transplantation, where the tissue match is not perfect, is the rejection of the transplanted organ via immunological response and destruction. Rejection can occur despite the routine immunosuppressive treatment given to transplant recipients.

Traditionally, heart transplants have been monitored for evidence of immunological rejection by taking tissue samples with a transvenous endocardial bioptome. The tissue samples are examined microscopically by a pathologist for evidence of tissue destruction. The disadvantages of this approach are that the monitoring technique is invasive (and therefore has inherent risks) and, importantly, a rejection event can be diagnosed only after there has been histologically detectable tissue damage.

Studies of endomyocardial biopsy specimens have included phenotypic characterization of mononuclear infiltrates, expression of MHC class I/II antigens, cell adhesion molecules, detection and/or quantitation of messenger RNA encoding cytokines, extracellular matrix proteins, and studies of the function, specific VβSTcR gene usage and donor-specific committed and precursor frequency analysis of mononuclear cell cultures from such biopsies. The recent recognition of a high degree of correlation between graft rejection and increased frequencies of in vitro-cultured graft-infiltrating cells that are anti-CD8 monoclonal antibody-resistant (high affinity) donor-specific cytotoxic T lymphocytes (CTL) in biopsy specimens has added another dimension to the diagnosis of allograft rejection [Ouwehand et al. (1993) Transplantation 56:1223–1229].

Noninvasive techniques for assessing the status of a transplanted organ have been summarized in Kemkes et al. (1992) J. Heart Lung Transplant. 11:S221–S231 and Miller et al. (1993) J. Am. Coll. Cardiol. 22.:41–54.

In the present invention, a rejection episode can be predicted or diagnosed via the increase in the frequency of Hprt-deficient mutant cells in the PBMC population at a time earlier than is possible by the conventional tissue biopsy and histological examination methods. This increase in frequency can be detected before the onset of significant tissue damage and, as a result, significant tissue damage can often be prevented by the early administration of immunosuppressive therapy. It is believed that the cost of the test is significantly less than that for the conventional tissue biopsy and, because the test is noninvasive, there are fewer risks to the patient. Moreover, as little as 1–2 ml of peripheral blood serves as a sufficient sample for the determination of an elevation in the frequency of Hprt-deficient cells in the PBMCs and, therefore, this technique is readily applied to pediatric as well as adult patients.

Hprt-deficient cells can be selected by growth in the presence of the nucleotide analog 6-thioguanine (6-TG). 6-TG is toxic to wild-type cells (those which produce functional Hprt).

Mutation in the gene encoding Hprt has been shown to occur preferentially in dividing T cells [Albertini et al. (1990) in Mutation and the Environment: Proceedings of the Fifth International Conference on Environmental Mutagens. M. L. Mendolsohn, Ed., Liss, New York, N.Y.]. The mutations can arise through errors in DNA replication, through inadequate DNA repair or by fixation of mutation. Thus, the frequency of mutant cells is enriched in cells which have recently divided in vivo. The frequency of Hprt-deficient cells in normal adults has been reported to be $5.4\pm4.8\times10^6$ [Albertini et al. (1982) Proc. Natl. Acad. Sci. USA 79:6617–6621; Albertini et al. (1985) Nature 316:369; Nicklas et al. (1987) Mutat. Res. 173:65; O'Neill et al. (1987) 2:87; O'Neill et al. (1989) Environ. Mol. Mutagenesis 13:289]. By contrast, multiple sclerosis patients have been demonstrated to have a statistically higher frequency of Hprt-deficient mutant PBMC population than normal adults, with patients with chronic disease having higher apparent mutant frequencies in peripheral blood than patients with the remitting form of the disease [Albertini et al. (1990) Science 247:718–721]. However, others have reported that there was not a higher incidence of Hprt-deficient mutant T cells in multiple sclerosis patients [Ammenhauser et al. (1988) Mutat. Res. 204:509; Seshadri et al. (1983) Mutat. Res. 110:141], but those studies used smaller sample sizes.

In the present study, the inventors have demonstrated the correlation between elevated incidence of Hprt⁻ mutant PBMCs and allograft rejection episodes where Hprt⁻ mutant cells are selected via their resistance to 6-thioguanine. Alternatively, Hprt⁻ PBMCs can be assessed by Multiplex Polymerase Chain Reaction Technology, also as described herein.

To ensure that the frequency analysis was based on statistically valid culture conditions, cells from patients and controls were cultured by limiting dilution in the presence and absence of 6-TG, and the frequencies were calculated on the fraction of microtiter culture wells that showed growth at each cell concentration. Data showed an excellent log-linear relationship between cell input and fraction of negative wells (data not shown), similar to the results published elsewhere [Gmelig-Meyling et al. (1992) J. Exp. Med. 175:297–300]. The cloning efficiencies ranged between 5% and 92% for normal controls and between 4% and 74% for the patients.

To evaluate this technique, aliquots of cryopreserved PBMC samples which corresponded with a rejection grade of 3 or greater were compared for the frequencies of $Hprt^-$ mutants/$10^6$ cells with the frequencies derived from a sequential series of PBMC samples from 5 patients with no history of rejection (the two extremes). In addition, PBMC samples from normal adult volunteers were included as controls. FIG. 1 shows that PBMC samples from normal controls (N=10) and patients with no history of rejection (grade 0, N=32) gave values $\leq 6$ FMC/$10^6$ input cells. In contrast, 19 of the 22 PBMC samples with rejection grades of 3 or greater gave values >6 FMC/$10^6$ cells, 14 of which gave values >20 FMC/$10^6$ cells. Of these, 11 gave values of >50/$10^6$ cells (range 146 to 46,982 FMC/$10^6$) (See FIG. 1). Statistical analysis of the data revealed that values of FMC/$10^6$ input cells on PBMC samples from normal controls (N=10) versus those from patients with no histological evidence of rejection (N=32) gave a p value of 0.9474 (not significant). However, the p value for data comparing samples from patients having grade 3 or higher rejection with samples from controls and from patients with no histological evidence of rejection (N =32) was <0.0001.

A further line of study utilized previously cryopreserved sequential PBMC samples from patients after transplantation. This study comprised a series of at least 6 consecutive specimens from 5 patients (patients 23 to 27, N=32) who had a recorded rejection grade of 0 post-transplant; a series of at least 10 consecutive specimens from 6 patients (total 64 specimens) who experienced a single rejection episode early post-transplant (less than 1 year after transplantation); a series of at least 7 consecutive specimens from 6 patients (total 56 specimens) who experienced a single rejection episode late post-transplant (greater than one year after transplantation); and a series of at least 10 consecutive specimens from 10 patients (total 141 specimens) who experienced multiple rejection episodes.

The data obtained on the 32 samples from patients 23 to 27 with no history of rejection are shown in FIG. 1. The profiles of data from sequential PBMC samples from the 6 patients (patients 1 to 6) who experienced a single rejection episode early post transplantation and from 6 patients who experienced a single rejection episode late post transplantation (patients 7 to 12) are illustrated in FIGS. 2A–2F and 3A–3F, respectively. Profiles of data from sequential PBMC samples of 10 patients (patients 13 to 22) who experienced multiple rejection episodes are illustrated in FIGS. 4A–4D and 5A–5F. Because the PBMC samples of 4 of these 10 patients (patients 13 to 16) with multiple rejection episodes gave a wide range of values, this could only be depicted using a log scale for the Y-axis (see FIGS. 4A–4D), whereas profiles of the data of the sequential PBMC samples from the other 6 patients (patients 17 to 22) who experienced multiple rejection episodes are shown in FIGS. 5A–5F, using a linear scale for the Y-axis.

As illustrated in FIG. 2A–2F, sequential PBMC samples from each of 6 patients who experienced a single rejection episode relatively early post transplantation, as defined by histologic grading of their corresponding biopsies, showed rising numbers of mutant cells (FMC/$10^6$) prior to the rejection episode. Although there is considerable variation in the absolute numbers of FMC/$10^6$ with samples from individual patients (e.g., samples from patients 1 and 2 show relatively lower FMC/$10^6$ values than do those from patients 3 to 6), in each case, an increase in the FMC/$10^6$ value correlates with the subsequent occurrence of a rejection episode. In addition, in 5 of these 6 patients, the PBMC sample immediately following the rejection episode showed a marked decrease in the FMC/$10^6$ value. In patient #3, this decrease was noted in the second sequential sample following the rejection episode. These decreases in FMC/$10^6$ values are secondary to successful immunosuppressive therapy.

Analysis of the profiles of FMC/$10^6$ values obtained from sequential PBMC samples of patients experiencing a single rejection episode relatively late after transplantation (patients 7 to 12), as compared with profiles of samples from patients with rejection early after transplant (patients 1 to 6) showed some differences. While the FMC/$10^6$ in samples preceding the rejection episode showed marked increases, which correlated with the subsequent occurrence of the rejection episode, the absolute number of FMC/$10^6$ was considerably higher in samples from patients 7 to 12 than in patients 1 to 6. While the value of the sample on day 1056 of patient #10 appears low, the precise value was 112 FMC/$10^6$ as compared to 12 FMC/$10^6$ in the preceding day 952 sample. Consistent with the findings of data from patients 1 to 6, samples from patients 7 to 12 immediately following the rejection episode showed a marked decrease in 5 of the 6 patients. The other important difference noted was that, in some cases (patients 8, 9, and 10), the increase in the FMC/$10^6$ value was noted 100 days or more prior to histologically diagnosed rejection. Without wishing to be bound by any particular theory, it is believed that this prolonged high frequency of putatively activated cells represents chronic immune activation whose effector function is regulated locally (in situ) by immune mechanisms and cellular infiltrates present in the donor allograft. A possible source of the activated T cells, which are detected over prolonged periods, is the sub-endothelial infiltrates (endothelialiris). Such infiltrates are often detected in EMB specimens, even in the absence of myocardial rejection. In each of the cases reported in this study, the FMC/$10^6$ cells eventually returned to values of <6 FMC/$10^6$ cells after histologically diagnosed rejection, most likely due to successful immunosuppressive therapy.

Another series of studies centered on analysis of sequential PBMC samples from patients experiencing multiple rejection episodes. The profiles of the data from sequential samples from the 10 patients are illustrated in FIGS. 4A–4D (log scale for Y-axis) and 5A–5F (linear scale for Y-axis). In addition to an increase in the FMC/$10^6$ cells prior to histologic rejection in each case (although some variation was noted), elevated values were maintained following the first rejection episode. These data are consistent with the patients being refractory to immunosuppressive therapy. For patient #13, samples following the second rejection episode, especially day 174 and beyond, continued to give high FMC/$10^6$ values. The patient eventually died on day 276. In the other 9 cases, the values of FMC/$10^6$ eventually returned to <10 FMC/$10^6$, providing evidence consistent with resolution of the rejection response.

To quantitatively express the profiles of FMC/$10^6$ values, we initially included all patients with rejection (N =22) and examined the trends (determined by robust linear regression slopes) in FMC/$10^6$ values for samples prior to the onset of initial rejection as compared to FMC/$10^6$ values from serial samples in patients without rejection (11.53±1.33 versus 0.13±0.09, p=0.002; by analysis of covariance and by Wilcoxon two-sample test). Values of FMC/$10^6$ decrease after successful immunosuppression for rejection (slope −5.38±1.12, p=0.0001, as determined by analysis of covariance and by Wilcoxon two-sample test compared with slopes prior to initial rejection). There was a highly significant association between the onset of first rejection and an increased rate of FMC/$10^6$ values (determined by the logistic regression method) (p=0.0001), after adjusting for age and gender. Based on the cross-validated error rate determined by Fisher's discriminant analysis, the correlation between a rising trend in FMC/$10^6$ values and the onset of histological rejection, as compared with the absence of histological rejection, was 81.8% and 100%, respectively.

For the subgroup of patients with recurrent rejection episodes (N=10), trends of FMC/$10^6$ values during recurrent episodes were significantly higher than with patients without rejection episodes (37.57±4.57 versus 2.75±0.51, p=0.0001 by Student's two independent sample t-test and by Poisson regression). Thus, a rise and/or consistent elevation of values of FMC/$10^6$ cells appears to be associated with incomplete immunosuppression and subsequent episodes of rejection. Trends of FMC/$10^6$ values during recurrent rejection episodes were also significantly higher than those that followed the last treated rejection episode (37.57±4.57 versus 10.24±1.35, p=0.004, paired t-test), consistent with FMC/$10^6$ values dropping after successful immunosuppressive therapy for rejection. In addition, a highly significant association between the recurrent rejection episodes and the maintenance of increased rates of FMC/$10^6$ values (determined by the logistic regression method) was noted (p=0.0003), after adjusting for age and gender. Based on the cross-validated error rate determined by Fisher's discriminant analysis, the correlation between an elevated trend in FMC/$10^6$ values and the occurrence of recurrent rejection and no rejection was 90% and 100%, respectively.

The phenotype of each of the mutant cultures (N=>2000), the donor helper T lymphocyte (HTL) and cytotoxic T lymphocyte (CTL) specificity, and cytokine profile (RT-PCR) have been determined. In brief, the data indicate that the Hprt-deficient mutants isolated from the PBMC of patients undergoing a rejection episode early post-transplant (<1 year) have a dominant CD8+phenotype, whereas Hprt-deficient mutants from patients in the late post-transplant period are predominantly CD4+. In addition, the frequency of donor-specific Hprt⁻ clones in samples from patients at the time of histologically recorded rejection was markedly lower than the frequency prior to rejection (Table 2). This was seen in the samples examined from patients experiencing a rejection episode, either early or late post transplant.

The noninvasive immunologic parameters that have so far been examined include the monitoring of levels of IL-2R [Young et al. (1991) J. Heart Lung Transplant 10:243–250], expression of transferrin receptors [Hoshinaga et al. (1988) J. Heart Transplant 7:198–204], quantitation of TNF-α levels [Jordan et al. (1993) J. Heart Lung Transplant 12:333–337], and studies aimed at quantitating the frequency of donor-specific helper T lymphocytes (HTL) and donor-specific cytotoxic T lymphocytes (CTL) by limiting dilution analysis (LDA) [Vaessen et al. (1994) Transplantation 57:1051–1059; Zanker et al. (1993) Transplantation 56:628–632; DeBruyne et al. (1993) Transplantation 56:722–727; Mathew et al. (1993) J. Clin. Invest. 91:900–906; Reinsmoen and Matas (1993) Transplantation 55:1017–1023; Goulmy et al. (1989) Transplantation 48:559–563]. The daily fluctuations of IL-2R and transferrin receptor levels and their lack of correlation with biopsy-based rejection episodes and lack of specificity in distinguishing infection from rejection have led to skepticism regarding the feasibility of replacing biopsy analysis with these indicators. However, such studies may be important adjuncts for making decisions regarding the institution of immunosuppressive therapy. High levels of serum TNF-α correlate with severe episodes of humoral but not cellular rejection [Jordan, S. C. (1993) J. Heart Lung Transplant. 12:333–337]. In regard to quantitative analysis of donor-specific HTL and CTL frequencies in the PBMC of transplant recipients, the majority of studies report a high correlation between prolonged graft survival and a decrease in donor-specific reactivity (donor-specific hyporesponsiveness) [Zanker et al. (1993) Transplantation 56:628–632; Mathew et al. (1993) J. Clin. invest. 91:900–906; Reinsmoen and Matas (1993) Transplantation 55:1017–1023; Thomas et al. (1977) Surgery 81:125–131; Goulmy et al. (1981) Transplantation 21:210–217; Pfeffer et al. (1981) Transpl. Proc. 13:1604–1606].

It has been reasoned that such decreased reactivity could be due to selective entrapment of donor MHC-specific clones within the graft, induction of "anergy" within the donor-specific T-cell clones in circulation, or other regulatory mechanisms. Analysis of our data on the unmanipulated recipient PBMC for donor-specific reactivity is generally consistent with these findings. The present inventors did not note any significant correlation between peripheral blood donor-specific HTL or CTL frequency and histological grades of rejection, as noted elsewhere [Goulmy et al. (1989) Transplantation 48:559–563]. There are, however, reports of an association between increased donor-specific HTL and allograft rejection [DeBruyne et al. (1993) Transplantation 56:722–727]. The concept of entrapment of donor-specific T-cell clones in the allograft has prompted studies of such graft infiltrating cells (GIL) for donor-specific frequencies and specificity. Data from such studies support the view that there is selective enrichment of donor-specific T-cell clones in grafted tissues [Mayer et al. (1985) J. Immunol. 134:258–264; Zeevi et al. (1986) Transplantation 41:620–626; Duquesnoy et al. (1987) Transpl. Proc. 19:2560–2563; Sell et al. (1992) J. Heart Transplant. 11:511–521; Hall and Finn (1992) Transplantation 53:1088–1099; Krams et al. (1992) Transplantation 53:151–156; Vaessen et al. (1994) Transplantation 57:1051–1059; Ouwehand et al. (1993) Transplantation 56:1223–1229]. Detailed analysis of cells cultured from allograft biopsies for donor-specific proliferative responses termed helper T lymphocytes (HTL), donor-specific-sensitized (committed) cytotoxic T lymphocyte (c-CTL), and those with potential to be cytolytic for donor MHC (p-CTL) has been carried out utilizing the paradigm by Orosz et al. [Orosz et al. (1989) Transplantation 47:189–194] for distinguishing such cells. These studies, of course, require biopsy specimens.

Figure 2A:
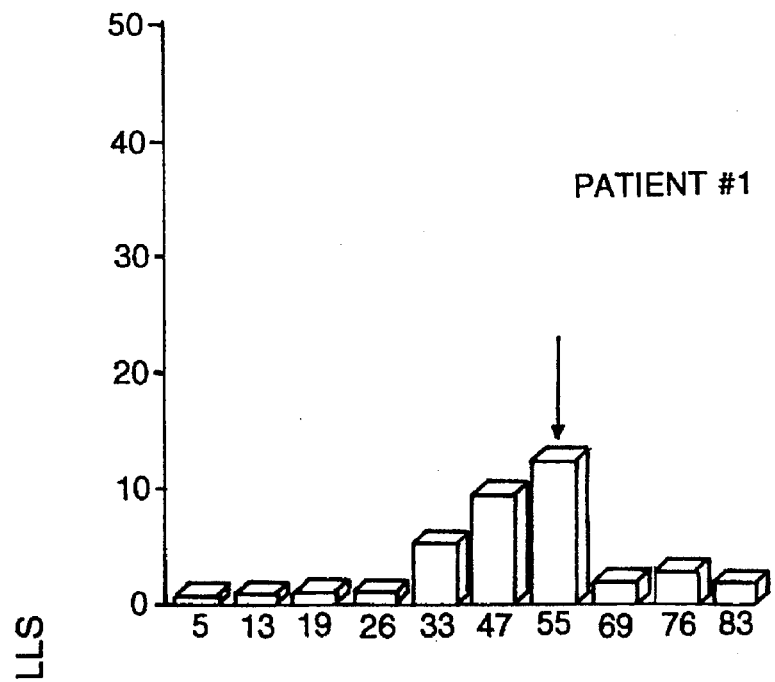
FIGS. 2A–2F present data for the frequency of Hprt-deficient PBMCs versus time after transplant in six transplant patients who experienced rejection during the early post-transplant period. Samples were taken sequentially in the time period around the single rejection episode. In each of FIG. 2A (patient #1), FIG. 2B (Patient #2), FIG. 2C (Patient #3), FIG. 2D (Patient #4), FIG. 2E (Patient #5) and FIG. 2F (Patient #6), the arrow indicates the day on which the rejection episode was diagnosed histologically after endomyocardial biopsy.
Figure 2B:
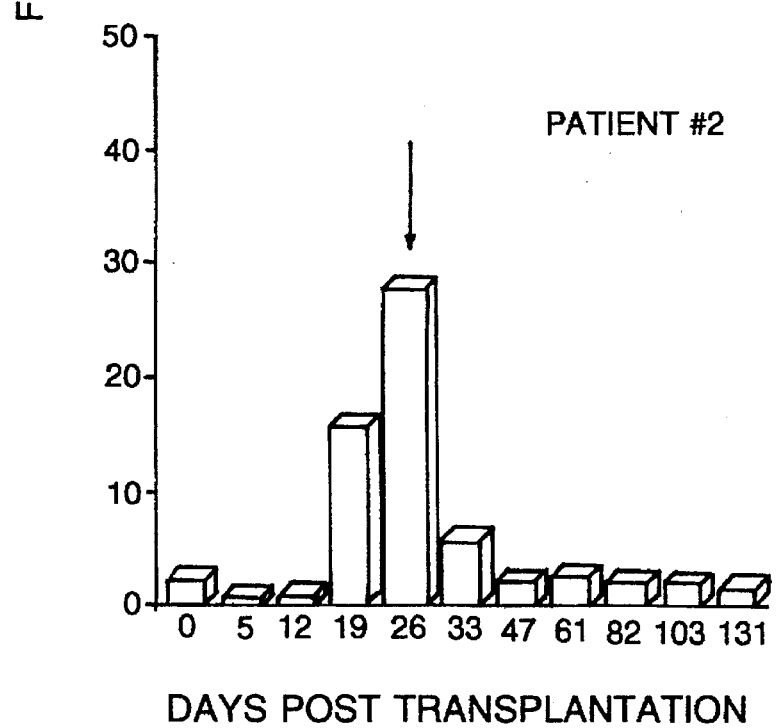
Figure 2C:
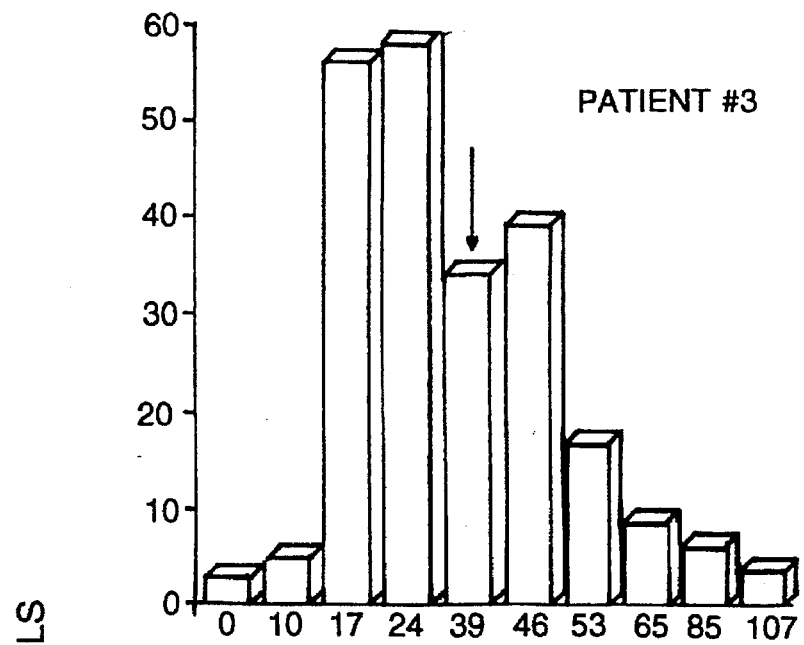
Figure 2D:
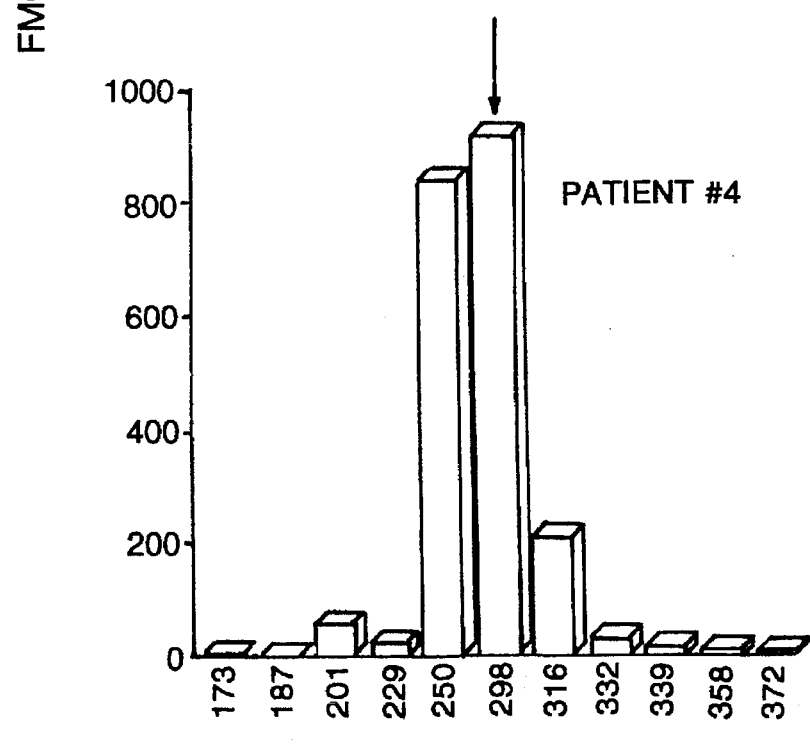
Figure 2E:
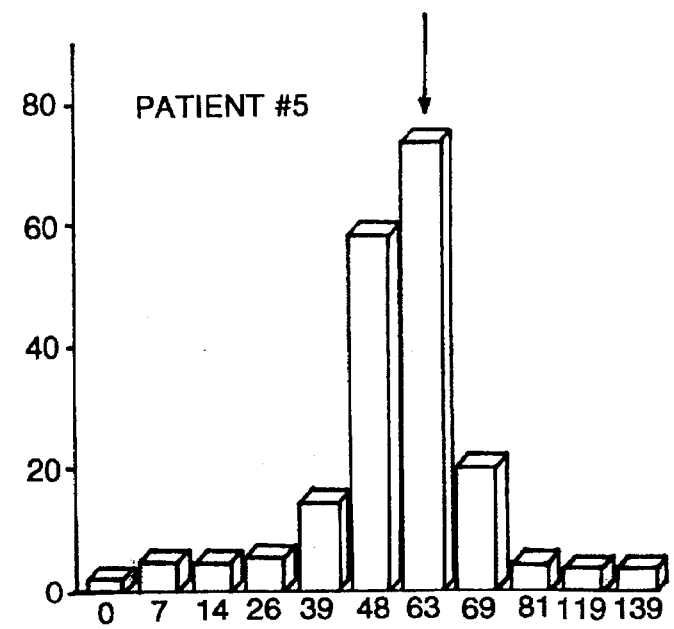
Figure 2F:
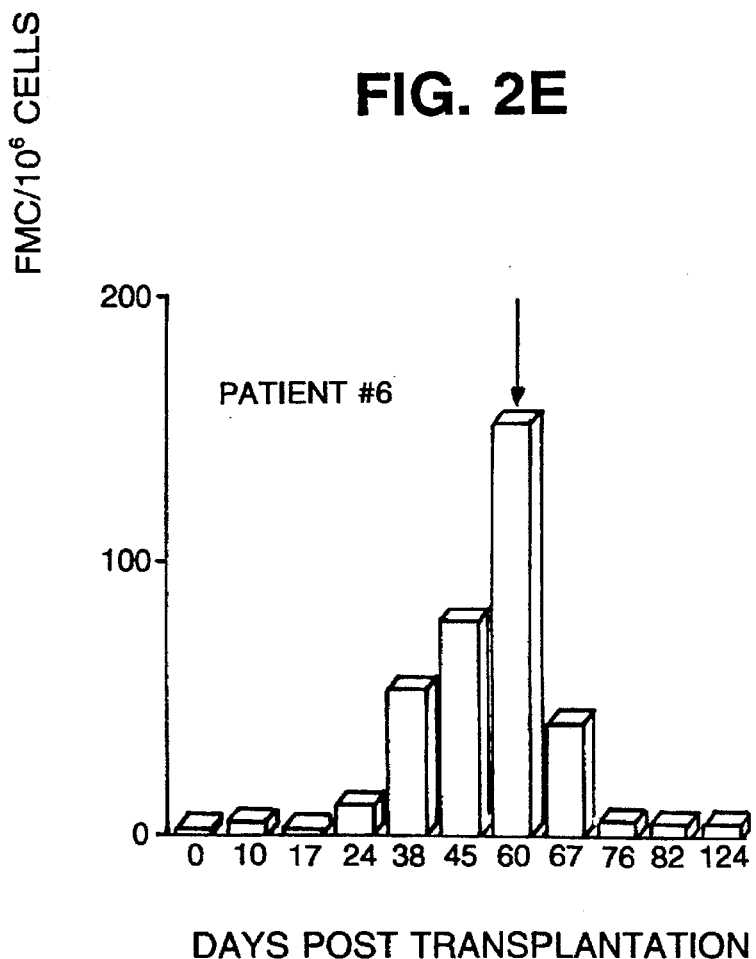
Figure 3A:
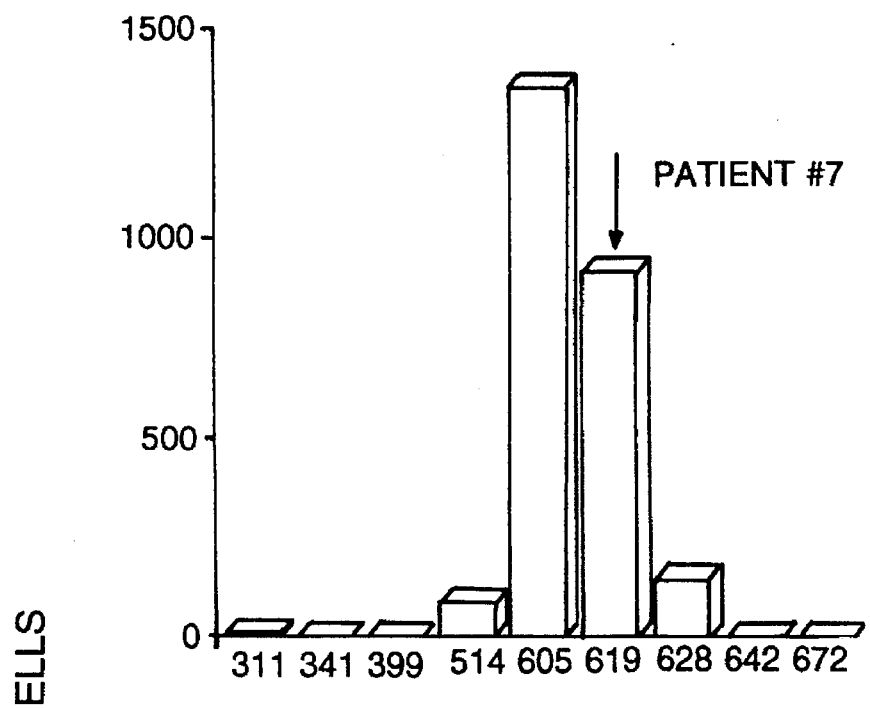
FIGS. 3A–3F present data for the frequency of Hprt-deficient PBMCs in sequential samples versus time after transplant in six transplant patients who experienced rejection during the late post-transplant period. In each of FIG. 3A (patient #7), FIG. 3B (Patient #8), FIG. 3C (Patient #9), FIG. 3D (Patient #10), FIG. 3E (Patient #11) and FIG. 3F (Patient #12), the arrow indicates the day on which the rejection episode was diagnosed histologically after endomyocardial biopsy.
Figure 3B:
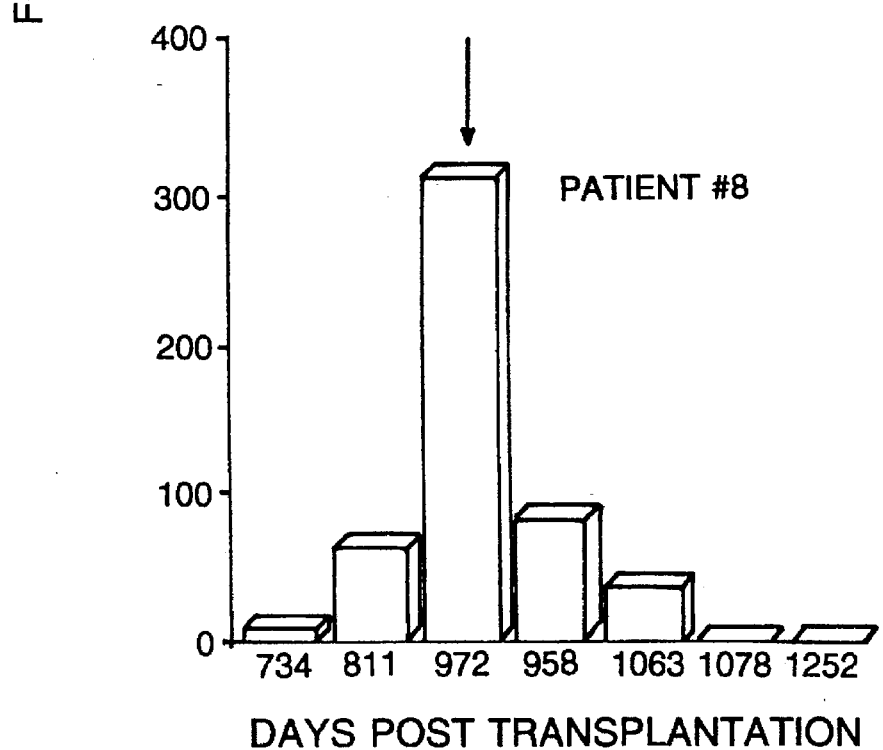
Figure 3C:
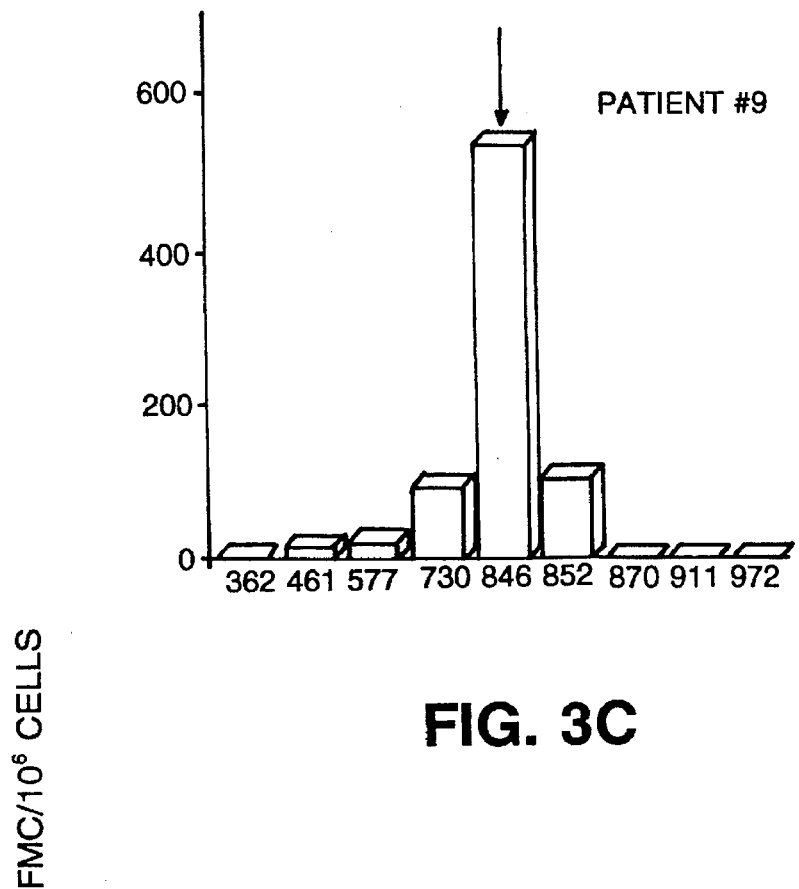
Figure 3D:
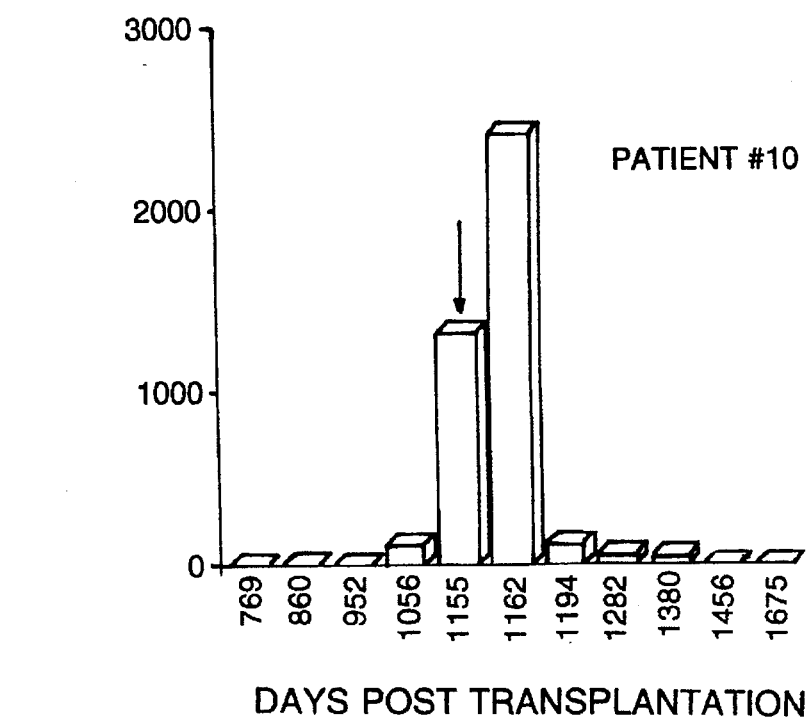
Figure 3E:
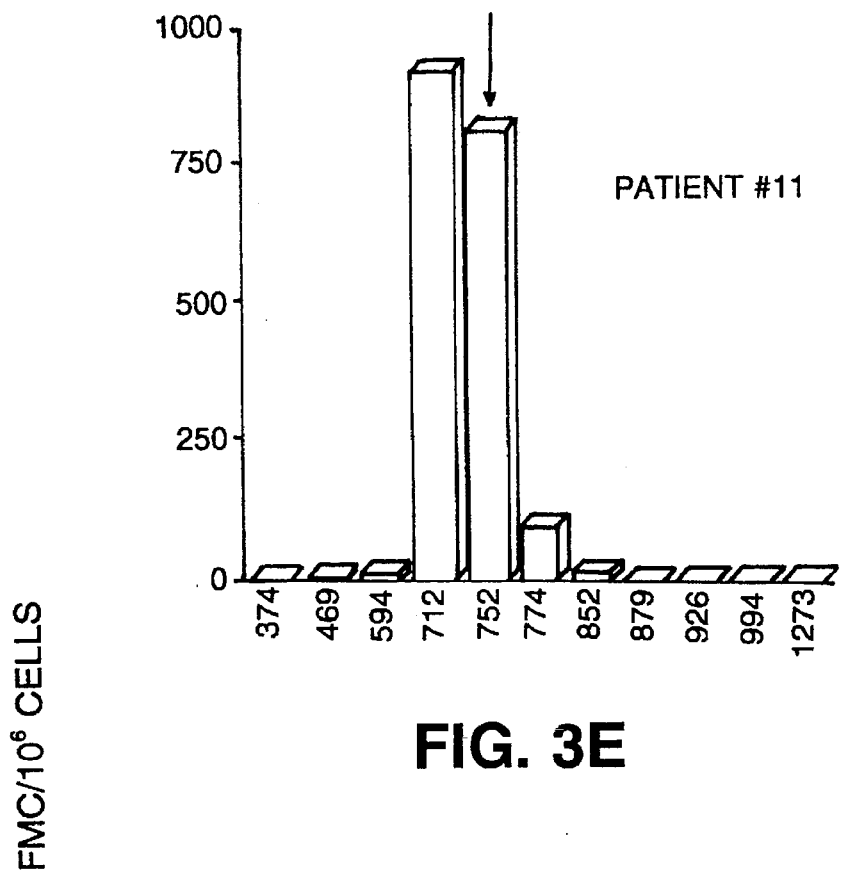
Figure 3F:
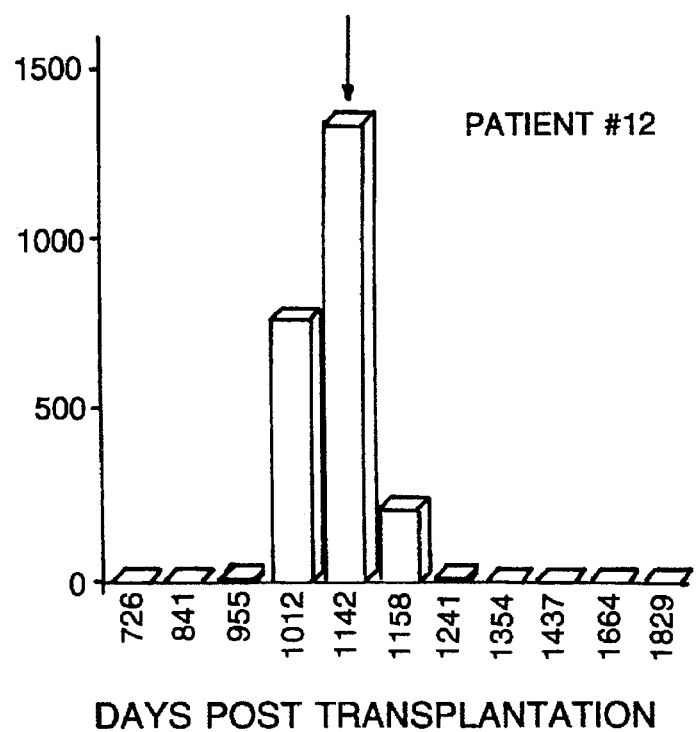
Figure 6A:
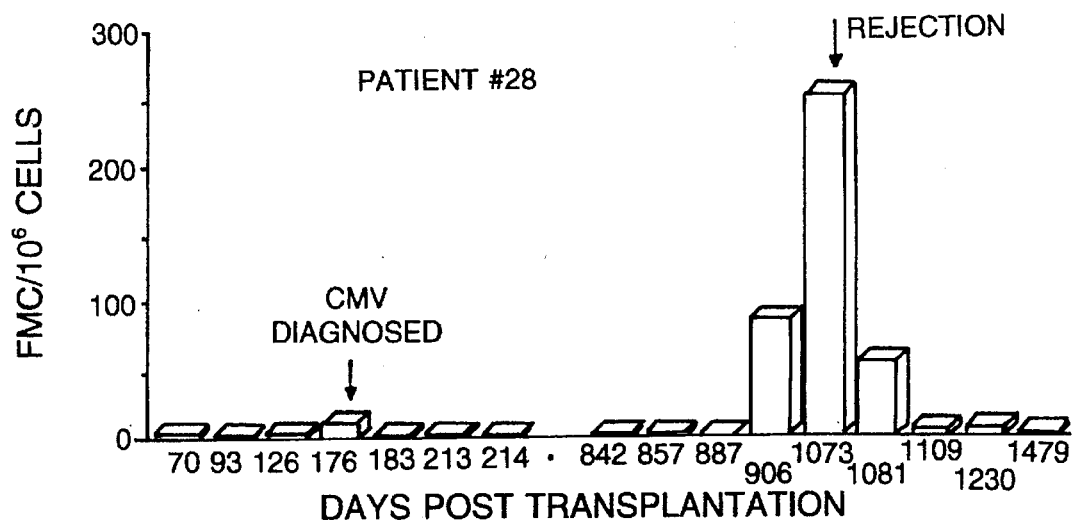
FIGS. 6A and 6B provide the frequencies of Hprt-deficient cells per $10^6$ cells for sequential PBMC samples from two patients (Patients #28 and #29, respectively) with cytomegalovirus (CMV) infection.
Figure 6B:
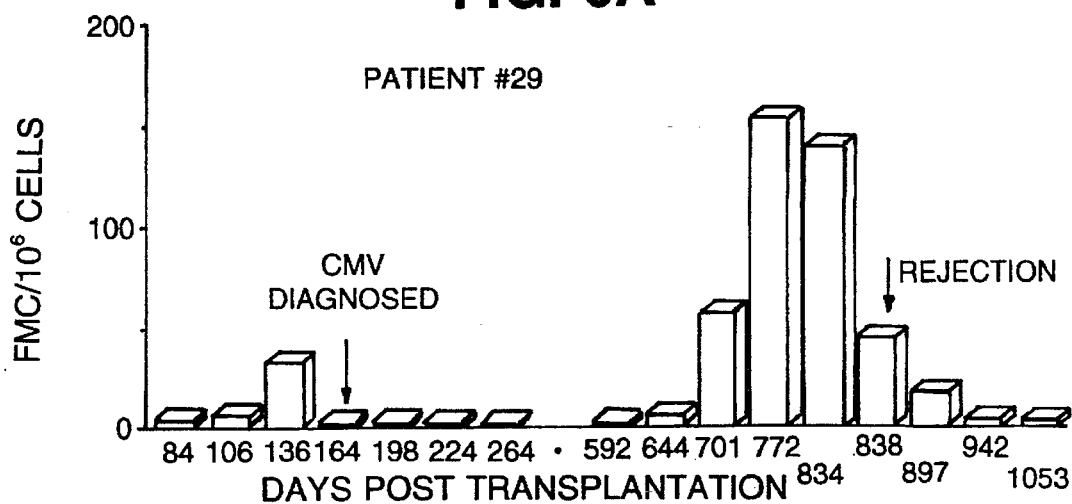
Figure 6C:
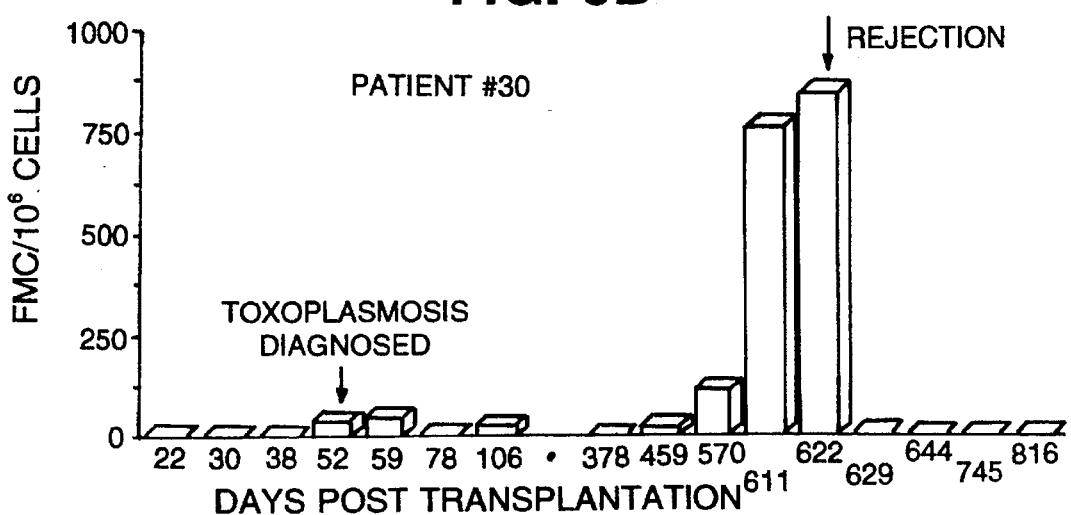
FIG. 6C presents similar results for Patient #30, who was diagnosed with toxoplasmosis 52 days after the heart transplant. CMV infection was diagnosed by increasing IgG anti-CMV titers, and, in one, by histological evidence of inclusion bodies in the endomyocardial biopsy tissue. PBMC samples included three samples prior to and 3 samples after diagnosis of infection and included sequential samples from the same patients who experienced a single treated rejection episode later post-transplant.

In regard to infection-related immune activation and allograft rejection, our laboratory has studied sequential PBMC samples from two patients with CMV (patients 28 and 29) and one patient with toxoplasma infection (patient 30), as documented by rising IgG antibody titers against CMV and histological diagnosis from EMB specimens in one CMV patient and the patient with toxoplasma infection. Cryopreserved PBMC specimens that included three sequential samples prior to and post diagnosis of infection and sequential samples from these patients at a later time post transplant (>6 months), when each experienced a histologic grade 3 rejection episode, were available. Thus, the FMC/$10^6$ cells from the same patient during infection and rejection were compared. The data derived from these studies confirmed that an increase in the frequencies of FMC/$10^6$ cells preceded the histological diagnosis of rejection in the endomyocardial biopsy specimen in each of the three patients studied. Second, the frequencies of Hprt-deficient mutant cells/$10^6$ PBMC were significantly higher during the rejection period in each case as compared with values of FMC/$10^6$ cells prior to, during, and following diagnosis of infection in each case (see FIGS. 6A–6C). It should be noted, however, that the FMC/$10^6$ cells during the infection period are significantly higher in samples from these patients (patients 28 to 30) than in those experiencing rejection episodes during the early post transplant period (FIGS. 2A–2C, Patients 1, 2 and 3). Thus, comparison of data among different patients may not be possible. However, it is possible that the proper distinction between infection and rejection, based on FMC/$10^6$ values, may be pertinent for only data derived from individual patients (relative increases). Third, comparative analysis of phenotype and cytokine profile of individual Hprt$^-$ clones obtained from samples at the time of diagnosis of infection with the sample obtained at the time of rejection revealed interesting differences. As shown in Table 3, the predominant Hprt$^-$ clones at the time of diagnosis of infection in all three patients were CD8+(75, 52.3 and 62.7, respectively) and synthesized TH1-like cytokines (58.3, 53.8, and 43.5%, respectively). In contrast, the Hprt$^-$ clones at the time of rejection were CD4+(71.89, 75.9, and 69.8%, respectively) and synthesized TH2-like cytokines (43.6, 61.9, and 32.6%, respectively). Independent of the frequency of mutant cells, it is possible to distinguish infection-related activation from rejection by using concordant sets of additional data, such as cell surface phenotype and cytokine profile, in combination with serological data and studies of the biopsy for the presence of infection.

Previous studies have focused on the effect of various forms of drugs and agents in inducing mutations, for example, the hprt gene in the PBMC of patients. These drugs and agents include steroids for the therapy of lupus [Gmelig-Meyling et al. (1992) J. Exp. Med. 175:297–300], antineoplastic agents, irradiation [Sala-Trepat et al. (1990) Mutagenesis 5:593–598], and addictive drugs [Henderson et al. (1986) Mutagenesis 3:195–200]. In addition, the possibility that the patients are carriers of a partial defect in the hprt$^-$ gene was entertained. In regard to the effect of drugs, immunosuppressive drugs may influence the frequency of Hprt$^-$ mutant cells, especially if they are effective on dividing cells. Values obtained for samples from patients in the late post transplant period are, in most cases, much higher than for samples from patients in the early post transplant period. Because all patients studied, including those experiencing no rejection, receive standardized immunosuppressive drug regimens, and because the frequencies of Hprt-deficient mutants in sequential samples from the same patient change, it is unlikely that the increase in mutant cell frequencies is due to drug therapy.

In regard to the nature and function of the Hprt$^-$ mutants, as noted above, our laboratory has cloned T-cell lines from the Hprt-deficient mutant cultures and the cloning efficiency cultures. The cloned T-cell lines have been phenotyped for both cell surface markers and cytokine profile. In addition, the frequency of cloned T-cell lines that demonstrate donor-specific proliferative and cytotoxic response have been characterized.

Figure 4A:
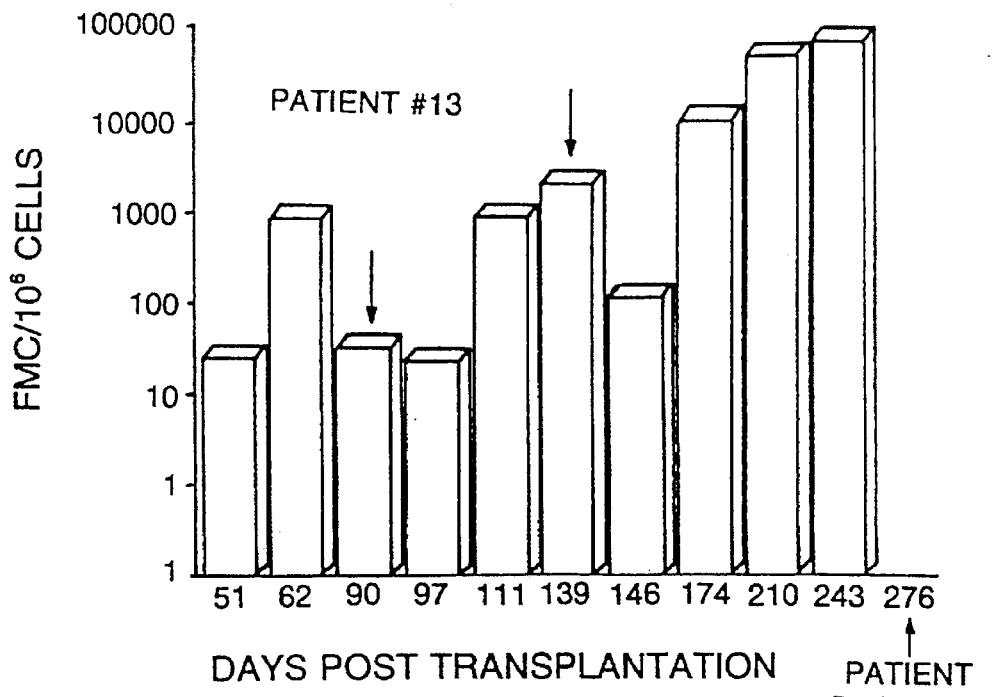
FIGS. 4A–4D illustrate the frequencies of Hprt-deficient PBMCs in sequential samples of four patients taken during time periods encompassing multiple rejection episodes as described in Example 1. Because the data from four patients (FIG. 4A, Patient #13.
Figure 4B:
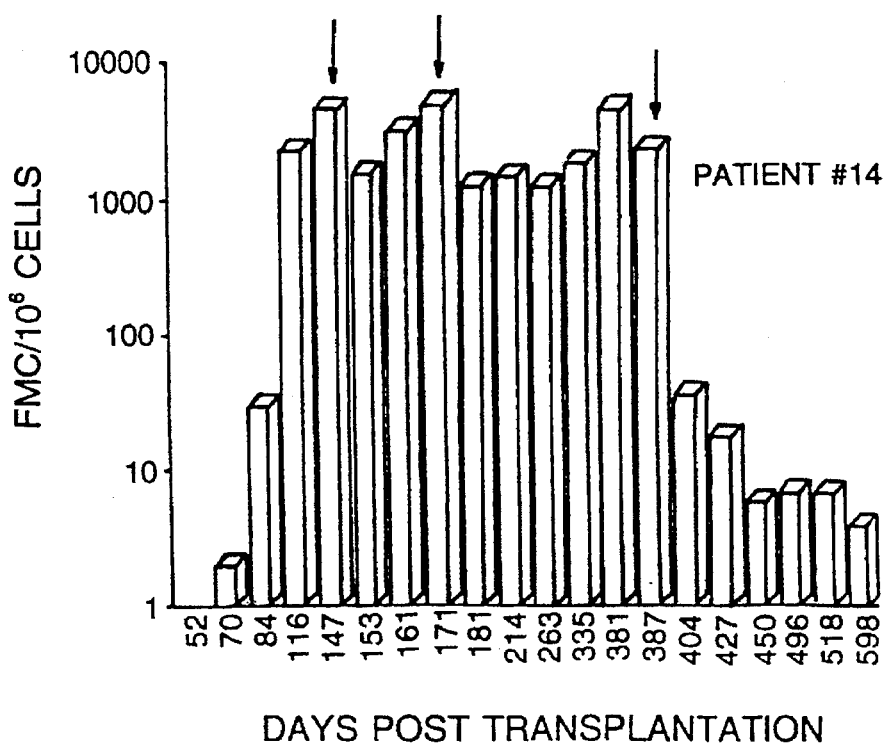
Figure 4C:
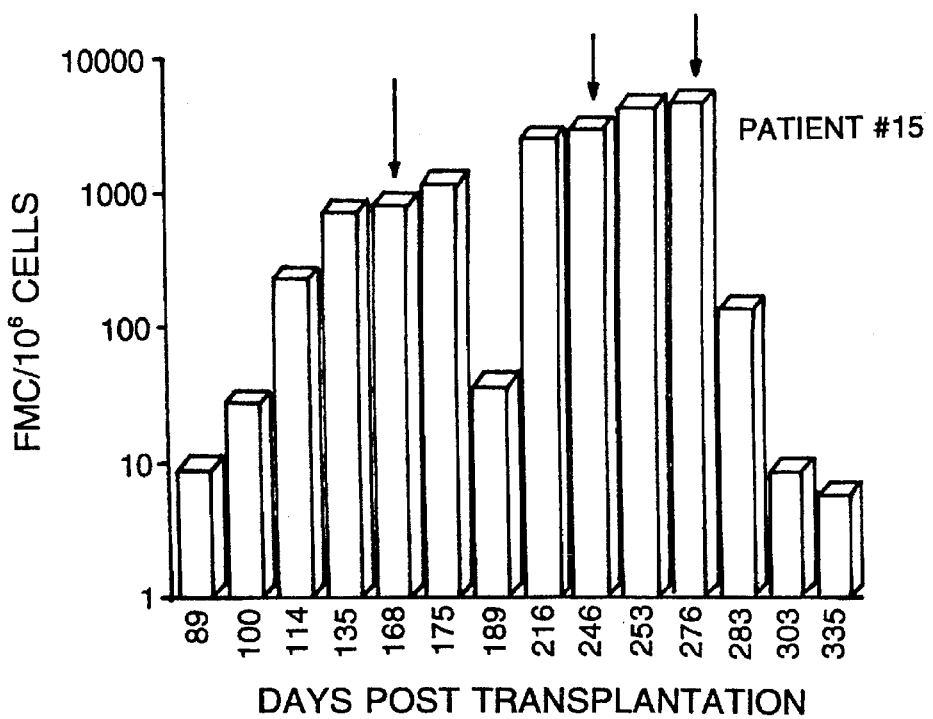
Figure 4D:
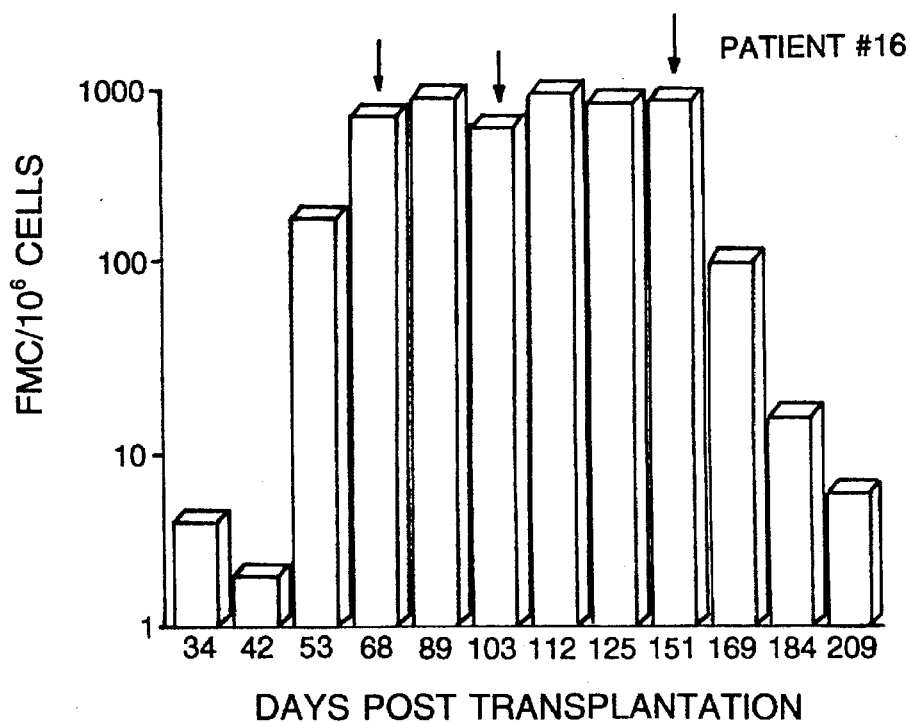
Figure 5A:
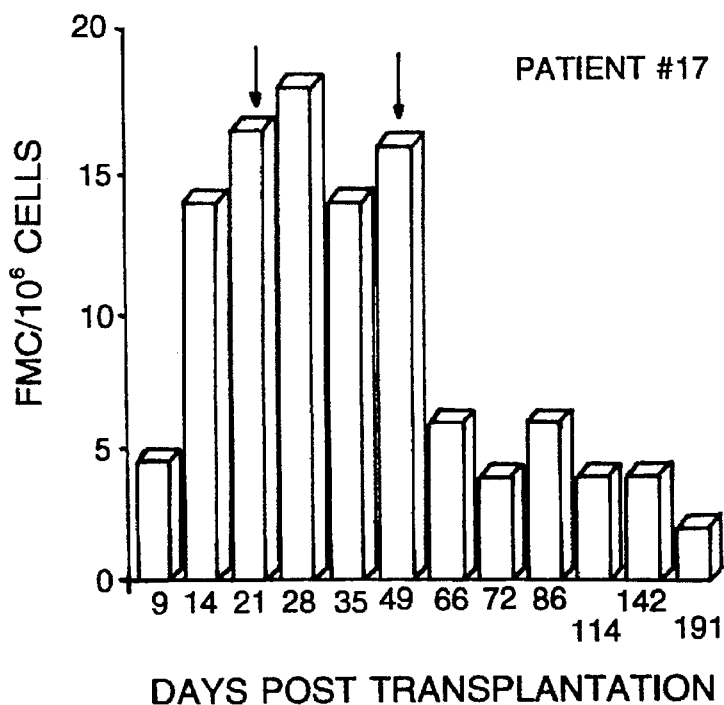
FIGS. 5A–5F illustrate the frequencies of Hprt-deficient PBMCs in sequential samples of patients (N=6) taken during time periods encompassing multiple rejection episodes as described in Example 1. The data for FMC/$10^6$ cells from samples of these six patients (FIG. 5A, Patient #17.
Figure 5B:
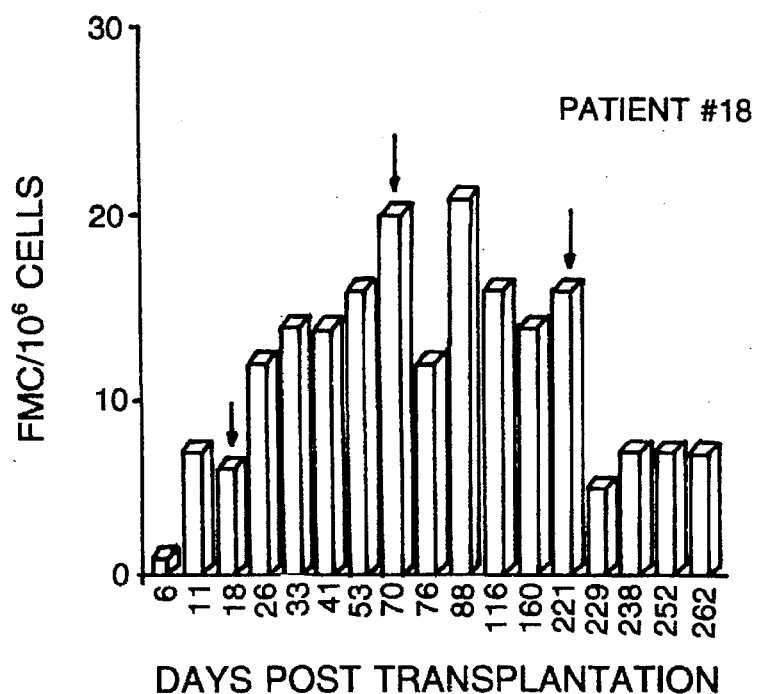
Figure 5C:
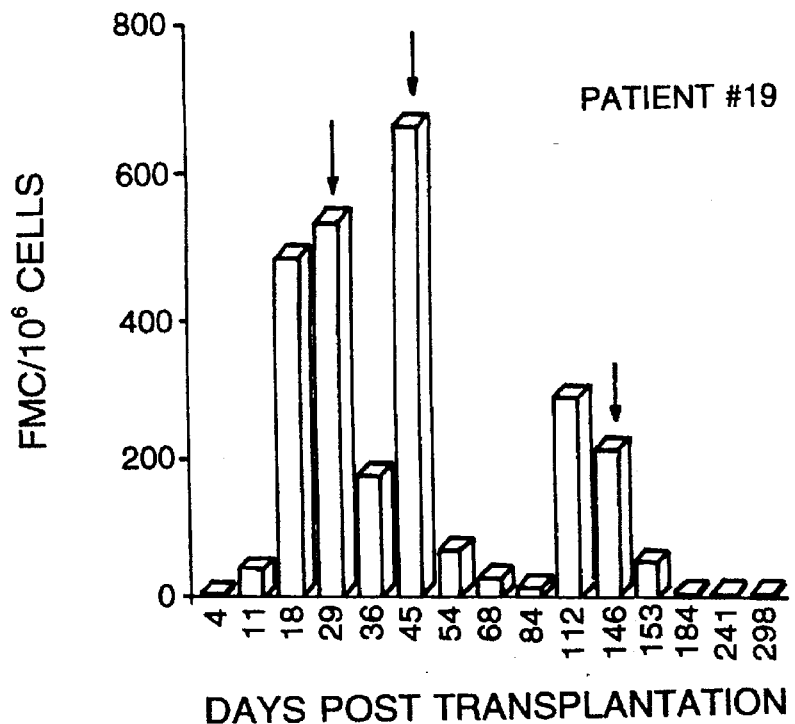
Figure 5D:
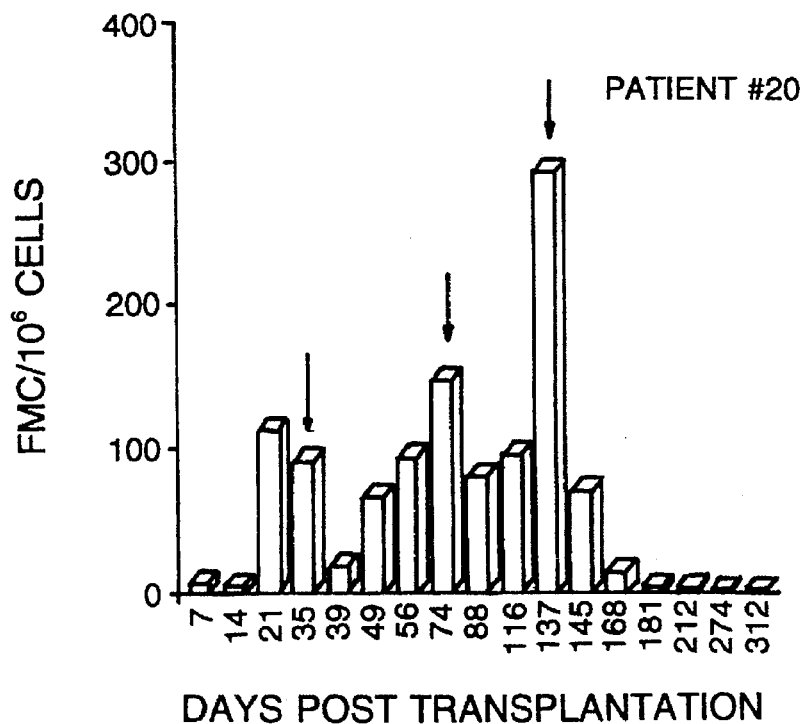
Figure 5E:
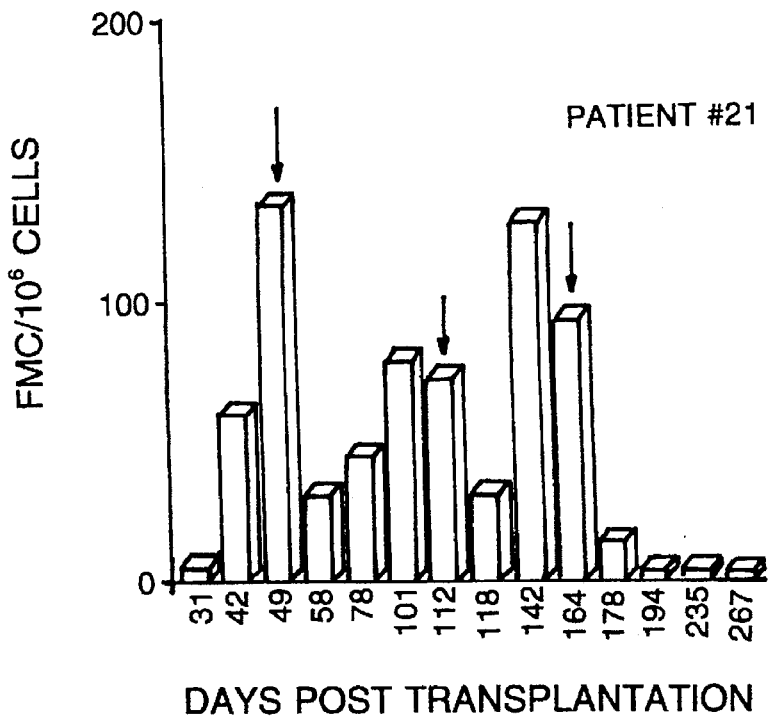
Figure 5F:
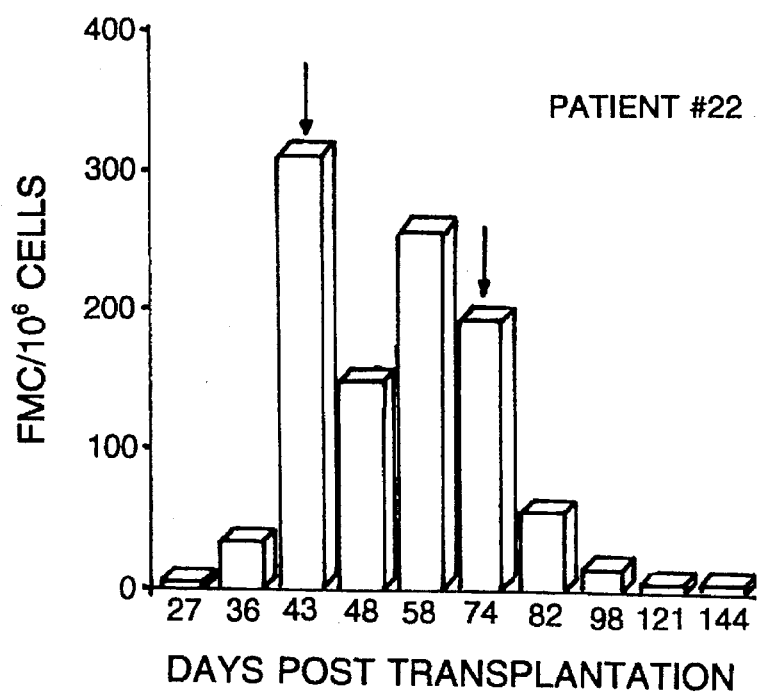

As seen in FIGS. 4A–4D and FIGS. 5A–5F, PBMC samples from some patients show prolonged increased frequency of Hprt$^-$ mutants, either prior to or following a rejection episode. While continued allogeneic stimulation which is insensitive to immunosuppressive drug therapy may account for continued increased frequencies of Hprt$^-$ mutants in patients with multiple rejection episodes, it is difficult to determine the reasons for such sustained increases in patients who experience a single rejection episode. It is possible that such increased in vivo activation represents host regulatory responses involved in graft "adaptation," which utilizes pathways of T-cell activation that are not sensitive to immunosuppressive drugs. Occurrence of sustained increased levels of Hprt-deficient mutant cells in the PBMC has also been noted in patients whose biopsies showed no evidence of rejection but who died secondary to accelerated graft atherosclerosis (AGA) post cardiac transplantation; sequential PBMC samples from these patients up to the time of their death showed >50 FMC/$10^6$ cells. Data from one such patient (patient #13) are shown in FIG. 4A.

Without wishing to be bound by any particular theory, the mechanisms by which the frequencies of Hprt$^-$ mutants eventually decrease may be related to the pathways utilized by T cells, the ratio of various T-cell subsets that are mediating rejection and their relative susceptibility to immunosuppressive drug therapy. If immunosuppressive drugs inhibit the maturation of donor-specific p-CTL to c-CTL and are not effective in inhibiting the effector function of c-CTL, the rejection response will continue until the frequency of c-CTL is exhausted. Semi-quantitative PCR techniques to detect the frequencies of Hprt$^-$ cells [Borreson et al. (1990) Prog. Clin. Biolog. Res. 340A:389–398] can provide data in a more timely fashion. Although an increased frequency of Hprt$^-$ cells in samples from patients up to 100 days prior to histologically diagnosed rejection could represent infection or rejection, careful monitoring of such patients is useful. Peripheral blood samples from three patients whose biopsies did not show any evidence of histological rejection had high sustained frequencies of Hprt-deficient cells in repeated samples up to six months prior to death secondary to accelerated graft atherosclerosis. However, for most patient evaluations, the present assay can be used prospectively. In addition, sensitive assays for serum cytokines can facilitate faster diagnosis of rejection. Determining the frequencies of Hprt$^-$ mutant cells in the PBMC of patients undergoing organ transplants other than heart can also be useful in predicting and/or diagnosing rejection.

Where PCR is used in the diagnosis or prediction of an allograft rejection episode, failure to amplify one or more exons using the primers disclosed in Table 5 is diagnostic of a mutation of the relevant exon(s). It is understood that where there are allelic variations in the sequences corresponding to the primers, the skilled artisan can use alternate primer sequences adapted for the allelic variations.

All references cited in this application are hereby incorporated by reference.

The following, non-limiting examples are intended to illustrate the invention as claimed. Modifications and variations which may occur to one of ordinary skill in the art are within the intended scope of this invention.

EXAMPLES

Example 1. Peripheral Blood Samples

A total of 27 adult patients undergoing cardiac transplantation at Emory University Hospital were the sources of peripheral blood samples which were analyzed in detail. Samples for analysis were chosen so as to constitute a series of consecutive samples from patients who experienced no rejection episode (N=5), patients who experienced a single rejection episode relatively early after transplant (arbitrarily chosen as 1 year after transplant), patients who experienced a single rejection episode relatively late after transplant (1 year, N=6) and patients who experienced multiple rejection episodes (N=10). All transplant recipients are routinely treated with immunosuppressive drug therapy which includes cyclosporin A, azathioprine and prednisone. Episodes of significant rejection, where biopsies indicated focal moderate, moderate or severe rejection, were treated with high-dose methyl-prednisolone or oral prednisolone, and in select cases of recurrent or severe rejection, with intravenous OKT3 monoclonal antibody. The mean age of the transplant patients was 48 years (range, 15–63). Donor/recipient MHC class I and class II typing results were available for each patient. Unless otherwise stated, the samples were selected from 27 patients with no history of infection and no detectable malignancy. Infection was defined by the presence of positive bacterial or fungal blood cultures or by serological or histologic evidence of viral infection (e.g., CMV) or protozoan infection (e.g., toxoplasmosis). Percutaneous transvenous endomyocardial biopsies were performed on cardiac transplant recipients within the first week, weekly for six to eight subsequent weeks and then according to a routine schedule or as clinically indicated.

Heparinized peripheral blood samples were routinely obtained at specified intervals from each patient undergoing cardiac transplantation at Emory University Hospital. These samples included those obtained prior to transplantation and at scheduled times post-transplantation when endomyocardial biopsies were also taken or when clinically indicated.

Peripheral blood and lymph node samples from each donor at the time of transplantation were also obtained. Peripheral mononuclear cells were separated by density gradient centrifugation. Donor mononuclear cells were incubated in vitro with supernatant fluid from the B95-8 marmoset cell line to determine Epstein Barr Virus (EBV)-transformed cell lines. Donor and recipient cells were typed for MHC class I and II antigens by the Tissue Typing Laboratory of Emory University Hospital. Aliquots of peripheral blood mononuclear cells (PBMCs) were cryopreserved at −196° C. in medium containing 7.5% DMSO and 20% pooled normal human AB plasma, and the samples were tracked using a computerized inventory. All procedures involving procurement of blood and tissue samples from patients were approved by the Human Investigations Committee of Emory University School of Medicine. An informed consent form was signed by each blood or tissue donor prior to sampling. PBMC samples from volunteer healthy laboratory personnel were used in some comparative studies.

Example 2. Histological Rejection Grades

Aliquots of the endomyocardial biopsy tissues were fixed in 10% neutral buffered formalin, processed in a rapid tissue processor in a 4-hour cycle, and embedded in paraffin as a single block. The biopsies were serially sectioned to provide slides at 16 levels. Every other slide was stained with hematoxylin and eosine (H&E) and microscopic evaluation was carried out. Intervening slides were used for special stains if deemed necessary. The grading of the biopsies was performed using a modification of the standardized histologic grading system devised by Billingham et al. [Billingham et al. (1990) J. Heart Transplant 9:587–592] as described by Ahmed-Ansari et al. (1988) Transplantation 45:972–978. Episodes of significant rejection, where the biopsy tissue exhibited focal moderate, moderate or severe rejection, routinely received additional immunosuppressive therapy.

Example 3. Cell Culture

To establish the frequency of Hprt-deficient mutant cells and to define the efficiency of cloning, PBMCs from patients and normal controls were cultured in vitro essentially as described [Albertini et al. (1982) Proc. Natl. Acad. Sci. USA 79:6617–6621; Allegretta et al. (1990) Science 247:718–720; Gmelig-Meyling et al. (1992) J. Exp. Med. 175:297–300]. The medium for enumerating the Hprt$^-$ cells was 47% RPMI 1640, 20% HL-1 medium (Ventrex Labs, Portland, Me.), 20% lymphokine-activated killer cell (LAK) supernatant fluid [J. R. Yanelli (1991) J. Immunol. Meth. 139:1–16], 10% heat-inactivated fetal calf serum (preselected lot from Hyclone Labs, Logan Utah), gentamycin (20 µg/ml), 2 mM L-glutamine, 25 µg/ml PHA (PHA-16 or PHA-17, Burroughs-Wellcome, Triangle Park, N.C.) and $1\times10^{-5}$ M 6-thioguanine (6-TG, 2-amino-6-mercaptopurine, Sigma Chemical Co., St. Louis, Mo.). A thymidine kinase-deficient (TK−) cell line was obtained from R. Albertini, University of Vermont, for use as a feeder layer. The cell line was routinely screened for mycoplasma, and repeatedly found negative. The TK− cell line was irradiated (8 Gy) using a $^{137}$Cs irradiation source (Gamma Cell 40, AEC of Canada, Ltd.), and $1\times10^5$ irradiated cells were dispensed in a volume of 0.1 ml of the above medium into individual wells of a 96-well microtiter plate. After 24 hours, frozen aliquots of PBMCs were thawed and washed. Then an aliquot of each was adjusted to $2\times10^5$ cells in the above-described medium. These cells were then dispensed in a volume of 0.1 ml into each well of a set of five microtiter plates containing the irradiated TK− feeder cells. A sixth microtiter plate containing only irradiated TK− feeder cells was included to control for reversion and survival of the 6-TG-resistant cells.

In no case was growth of the feeder cells cultured alone observed during the 14-day study. The microtiter plates were incubated at 37° C. in a humidified 7% $CO_2$ incubator and were observed microscopically for cell growth at specified time intervals. Positive, fast-growing wells were scored at 5, 7 and 10 days after inoculation and distinguished from those that showed visible growth at 14, 21 or 28 days. Positively growing cells were expanded and cloned by limiting dilution assays (LDA) and used for phenotypic analysis, donor specificity and cytokine profile testing. In the cases where all wells containing 6-TG and $2\times10^4$ cells showed growth, an aliquot of the same PBMC sample was diluted and the assay was repeated using 2, 20 or 200 cells per well to more precisely determine the frequency of Hprt-deficient mutant cells.

An aliquot of each PBMC sample was also analyzed for cloning efficiency (CE). The medium used for determination of CE was identical to that described above except that it did not contain 6-TG. The PBMC concentrations were adjusted to yield 0.5, 1, 2, 4 and 8 cells/0.1 ml, and a single 96-well plate was used for each cell concentration. Each microtiter well contained $1\times10^5$ irradiated TK− feeder cells as described above. The microtiter plates were incubated as above and the cells from wells showing positive growth at the lowest cell concentration for each sample were expanded and used for phenotypic analysis, donor specificity and cytokine profile analysis.

Generally, an entire series of PBMC samples from a single patient were assayed simultaneously. An aliquot of a cryopreserved large pool of PBMC (obtained by leukopheresis of a normal adult donor) was thawed and assayed with each analysis; this served as a control on inter-assay variability. The frequency of mutant cells and CE obtained with this control remained constant to within 10% S.D.

Example 4. Frequency-of-Mutant(FMC) Analysis

Assuming that the limiting dilution analysis of clonable cells follows a Poisson distribution, the FMC was established by dividing the apparent frequency of 6-TG-resistant cells by the cloning efficiency as follows: FMC=[−ln (fraction of negative wells in the presence of 6-TG)/number of lymphocytes per cell/CE]; CE=[−ln (fraction of negative wells in the absence of 6-TG/number of lymphocytes per well][Gmelig-Meyling et al. (1992) supra]. The standard analysis utilized $2\times10^4$ PBMC per microtiter well in medium containing 6-TG. In several cases, all 5 microtiter plates had positive growth in each of the 96 wells (i.e., 480 positive wells containing $2\times10^4$ cells/well or approximately >50 per $10^6$ cells cultured). In efforts to determine the precise frequency of mutant cells per $10^6$, an aliquot of the same PBMC sample was further analyzed using log dilutions of $2\times10^4$ (i.e., $2\times10^3$, $2\times10^2$, etc).

LAK cell medium is prepared for use in this assay; normal PBLs at 2 million per ml are cultured for 3 days at 37° C., 7% $CO_2$ in RPMI 1640, gentamycin, L-glutamine, 10% heat-inactivated fetal calf serum, 1000 U/ml recombinant interleukin 2 and then the cells are discarded after centrifugation. The conditioned medium is then frozen at −70° C. in aliquots of 20 to 50 ml.

To make the 100 ml medium for the selection, one mixes 47 ml RPMI 1640 medium, 20 ml HL-1 Medium (Ventrex), 20 ml LAK medium, 10 ml heat-inactivated fetal calf serum, 100 μl of 20 mg/ml gentamycin, 1 ml of 2.5 mg/ml Phytohemagglutinin (Burroughs Wellcome HA-16 or HA-17) stock solution and 6-TG at a final concentration of 50 μM. For selection plates, the PBMCs are separated from the patient's blood sample using Histopaque (specific gravity 1.078, Sigma Chemical Co., St. Louis, Mo.), or an equivalent composition, the cells are washed twice, and the cells are then suspended at a concentration of 200,000 cells/ml. An aliquot of 100 μl is reserved for the determination of cloning efficiency. To the remainder of the cell suspension, 6-thioguanine is added to a concentration of 2 μM. Aliquots of 100 μl each are added to 100 μl of cell suspension in the wells of microtiter plates. Wells are examined for cell growth on day 7 after inoculation and every 3–4 days thereafter. The number of wells with growth and no growth are recorded.

Example 5. Phenotypic, donor specific and cytokine profile analyses

Each cloned T-cell line was phenotyped using flow microfluorimetry (FMF) [Ahmed-Ansari et al. (1988) Am. J. Cardiovasc. Path. 2:193–210]. Analysis of donor-specific cytotoxic and proliferative responses using $^{51}Cr$-labeled donor EBV-transformed and third party non-MHC-related EBV-transformed target cell lines is carried out. [Ahmed-Ansari et al. (1988) supra; Sell et al. (1992) J. Heart Transplant 11:500–510.]

RNA was extracted from each cloned T-cell line and assayed for the presence of mRNA encoding a battery of cytokines as described in Villinger et al. (1994) Cytokine 5:469–480 in an effort to distinguish the TH1 and TH2 T-cell phenotypes. The presence of mRNA encoding Interferon-gamma but not Interleukins 4 or 6 was taken as evidence for a TH2-type clone.

Example 6. Statistical Analysis

Objectives of the statistical analyses described herein were to determine the reproducibility of the method used to determine the frequency of Hprt-deficient cells (expressed as FMC/$10^6$ cells), to quantify the time profiles of FMC/$10^6$ cells in serial samples among transplant patients, to determine the associations of those profiles with both the onset of the first rejection episodes and, in appropriate patients, the recurrence of rejection episodes, and to compare values of FMC/$10^6$ cells obtained from normal control volunteers, transplant patients with histology grades of 0, and transplant patients with grades of 3 or greater. The five patients who did not experience rejection served as the control group. FMC/$10^6$ values obtained within ten days of treated rejection episodes were excluded from the analysis due to the possibility that the results could be influenced by the immunosuppressive therapy. Separate models were applied to analyze the onset of an initial rejection episode and the recurrence of rejection episodes.

To evaluate the reproducibility of the FMC measurements at high and low frequency levels, repeated measure analysis of variance was applied after obtaining square root transformations of the frequency data. Estimates of measurement error variance (termed repeatability) and the 95% confidence intervals of reliability coefficients were determined for the repeated observations as described [Winer (1971) in Statistical Principles in Experimental Design, McGraw-Hill, New York, N.Y.; Shedecor and Cochran (1980) Statistical Methods, The Iowa State University Press, Ames, Iowa]. Overall agreement among repeat determinations of FMC/$10^6$ values were summarized using the Friedman's chi-square test.

For initial rejection episodes, the rising trend of FMC/$10^6$ values over sequential samples, leading up to the first rejection episode, was quantified by fitting a robust regression line to the data collected for each patient [Mosteller and Tukey (1977) in Data Analysis and Regression, Addison-Wesley, Reading, Mass.]. Time profiles so determined were then used as data points in subsequent analyses. To compare these robust time profiles in patients with and without rejection, the analysis of co-variance method and the Wilcoxoh's two-sample test were applied. The association between the onset of first rejection episodes and an increased rate of FMC/$10^6$ values was examined using the logistic regression and Fisher's discriminant analyses [Gnanadesikan, R. (1988) Methods for Statistical Data Analysis of Multivariate Observations, John Wiley and Sons, New York, N.Y.]. The cross-validated error rate of discrimination, which provides the percent correct rate for identifying onset of rejection episodes between normal patients and those with rejection, was also determined in the discriminant analysis.

For patients with recurrent episodes of rejection, the maintenance of high levels of FMC/$10^6$ values after the onset of the initial rejection episode was analyzed. A longitudinal model to Poisson count data was first used to determine the association between FMC/$10^6$ values and recurrent rejection [Liang and Zeger (1986) Biometrika 73:13–22]. The mean FMC/$10^6$ values during recurrent rejection events were compared with the means determined for control patients using the Student's two independent sample t-test. Similarly, the mean FMC/$10^6$ values calculated from the recurrent rejection episodes were contrasted with those determined after the last repeated rejection episode by the paired t-test. The efficacy of using FMC/$10^6$ values to discriminate between normal patients and those with recurrent rejection episodes was evaluated by the cross-validated error rate determined by the Fisher's discriminant analysis method.

Comparisons of FMC/$10^6$ values in peripheral blood samples from patients with histological rejection grade 0 and rejection grade 3 versus values from control normal volunteers were made using an ANOVA followed by a Fisher's PLSD. A p value of <0.05 was considered statistically significant.

Example 7. PCR-SSCP Analysis of Hprt$^-$ Mutant PBMCs

Aliquots of freshly prepared PBMCs are lysed and DNA samples are prepared from the lysates as described in Gibbs et al. (1990) Genomics 7:235–244. The DNA samples are analyzed for mutations in the hprt gene using multiplex PCR (See Table 5, 8 primer pairs to cover all 9 exons; single tube per sample). Single strand conformation polymorphism (SSCP) analysis is utilized to differentiate mutant DNA preparations [Gibbs et al. (1990) supra]. An aliquot of the amplification reaction is then electrophoresed in SSCP loading buffer and the material is size-separated by electrophoresis over a polyacrylamide gel (10%). The gels are stained with SYBR green (Trademark of Stratagene, La Jolla, Calif.) and the amplification product bands are visualized and photographed under ultraviolet light. The relative intensities of the bands are scanned and the ratios from mutant/normal amplicons are determined.

The complete sequence of the human Hprt locus is given in Edwards et al. (1990) Genomics 6:593–608.

TABLE 1

| Patient # | Days post-transplant | FMC/$10^6$ cells* | | | Mean ± S.D. |
|---|---|---|---|---|---|
| | | Test 1 | Test 2 | Test 3 | |
| A. Reproducibility of data from aliquots of the same PBM of transplant recipients set up on different days (low Hprt$^-$ frequency samples) | | | | | |
| CM094 | 164 | 3.5 | 4.6 | 3.8 | 3.97 ± 0.57 |
| CM128 | 19 | 1.2 | 1.3 | 1.4 | 1.3 ± 0.1 |
| CM150 | 21 | 8.0 | 8.5 | 9.6 | 8.7 ± 0.82 |
| CM174 | 88 | 5.0 | 6.5 | 4.8 | 5.4 ± 0.93 |
| CM180 | 621 | 1.0 | 1.0 | 2.0 | 1.3 ± 0.58 |
| CM187 | 362 | 8.0 | 6.5 | 6.8 | 7.1 ± 0.79 |
| CM187 | 870 | 3.0 | 4.0 | 3.0 | 3.3 ± 0.58 |
| B. Reproducibility of data on aliquots of the same PBMC sample from transplant recipients set up on different days (High Hprt$^-$ frequency samples) | | | | | |
| CM094 | 605 | 1260 | 1345 | 1298 | 1301 ± 42.5 |
| CM107 | 531 | 33 | 21 | 37 | 30.3 ± 8.3 |
| CM107 | 622 | 22 | 29 | 15 | 22 ± 7 |
| CM187 | 577 | 25 | 21 | 22 | 22.67 ± 2.1 |
| CM187 | 870 | 32 | 26 | 37 | 31.67 ± 5.5 |
| CM207 | 133 | 49 | 38 | 44 | 43.67 ± 5.51 |
| CM254 | 275 | 34.8 | 29.2 | 37.6 | 33.87 ± 4.28 |
| CM254 | 429 | 21.3 | 15.9 | 26.4 | 21.2 ± 5.25 |
| CM304 | 100 | 28 | 24 | 29 | 27.0 ± 2.65 |
| CM340 | 459 | 30 | 36 | 32 | 32.67 ± 3.1 |

*FMC = Frequency of mutant cells, which was calculated as described in Methods.

TABLE 2

Comparison of frequencies of donor-specific Hprt$^-$ clones obtained from PBMC samples prior to and during rejection episodes early and late post transplant*

| Patient # | Days post transplant | Donor-specific (%) |
|---|---|---|
| 3 | 17 | 12/56 (21.4) |
| | 24 | 18/58 (31.0) |
| | 39 | 4/34 (11.8) |
| 4 | 229 | 5/27 (18.5) |
| | 250 | 24/200 (12.0) |
| | 298 | 6/25 (3.0) |
| 7 | 577 | 6/25 (24.0) |
| | 730 | 18/94 (19.1) |
| | 846 | 16/200 (8.0) |
| 8 | 1056 | 29/112 (25.9) |
| | 1155 | 11/200 (5.5) |

*The Hprt$^-$ clones from patients who experienced a single rejection episode early (patients 3 and 4) and late (patients 7 and 8) post transplant were assayed for donor-specific proliferative response. Histologically diagnosed rejection was recorded on days 38, 298, 846 and 1155 post transplant in patients 3, 4, 7 and 8, respectively.

TABLE 3

Distinct phenotype and cytokine profile of Hprt$^-$ cloned T-cell lines from patients during infection compared with rejection.

| Pt. #[1] | Days post Tx[2] | Frequency (%)[3] | | | | | |
|---|---|---|---|---|---|---|---|
| | | Phenotype[4] | | | Cytokine pattern | | |
| | | CD4+ | CD8+ | CD56+ | TH0 | TH1 | TH2 |
| 28 | 176 | 8.3 | 75.0 | 16.7 | 33.3 | 58.3 | 8.3 |
| | 1073 | 71.8 | 21.3 | 6.9 | 54.4 | 2.0 | 43.6 |
| 29 | 136 | 41.1 | 52.3 | 6.6 | 38.0 | 53.8 | 8.2 |
| | 834 | 75.9 | 19.3 | 4.8 | 30.5 | 7.6 | 61.9 |
| 30 | 52 | 23.0 | 62.7 | 14.3 | 45.6 | 43.5 | 10.9 |
| | 622 | 69.8 | 17.4 | 12.8 | 55.6 | 11.8 | 32.6 |

[1] The Hprt$^-$ cloned T-cell lines (a) from patient #28 obtained on day 176 (n = 12) and day 1073 (n = 252), (b) from patient #29 obtained on day 136 (n = 32) and day 834 (n = 139), and (c) from patient #30 obtained on day 52 (n = 40) and day 622 (n = 200 of the 844) were utilized for phenotypic and cytokine profile analysis.
[2] Days 176, 136, and 52 represented days on which infection was diagnosed in patients 28, 29, and 30, respectively. Days 1073, 834, and 622 (after transplant) represent samples coinciding with the occurrence of rejection episodes in patients 28, 29 and 30, respectively (see FIG. 6A–6C and description for other details on data from these patients.) All day numbers are after transplant.
[3] Aliquots of each of the Hprt$^-$ cloned T-cell lines were subjected to phenotypic analysis by standard microfluorometry. Another aliquot was subjected to analysis of cytokine mRNA by using RT-PCR procedures [Ansari et al. (1994) J. Med. Primatol. 23:102–107]. Clones that synthesized IL-gamma but not IL-4/IL-6 were classified as TH1. Clones that synthesized IL-4/IL-6 but not IFN-gamma were classified as TH2, and clones whose cytokine pattern was indistinguishable were classified as TH0.
[4] Cells were phenotyped as either CD4+, CD8+, or CD56+. Those that were CD4+, CD8+(DP); CD4$^-$; CD8$^-$(DN); and/or other than CD4+, CD8+, or CD56+ were excluded from the analysis of frequencies.

TABLE 4

Kinetics of Hprt$^-$ mutant T-cell growth from PBMC of samples with high and low frequency of mutants

| Sample # | Frequency of positive cells | | |
|---|---|---|---|
| | Day 5 | Day 7 | Day 10 |
| 1 | 21 | 74 | >100 |
| 2 | 10 | 65 | >100 |
| 3 | 20 | 78 | >100 |
| 4 | 19 | 75 | >100 |
| 5 | 14 | 64 | >100 |
| 6 | 0 | 1 | 1 |

TABLE 4-continued

Kinetics of Hprt⁻ mutant T-cell growth from PBMC of samples with high and low frequency of mutants

| Sample # | Frequency of positive cells | | |
|---|---|---|---|
| | Day 5 | Day 7 | Day 10 |
| 7 | 0 | 3 | 2 |
| 8 | 0 | 1 | 2 |
| 9 | 0 | 1 | 3 |
| 10 | 0 | 1 | 3 |

*Aliquots of PBMC from samples that previously showed >50 FMC/10⁶ from 5 different patients (samples 1–5) and samples (6–10) that previously showed <6 FMC/10⁶ were assayed using the same general techniques described herein, and the kinetics of cell growth of individual wells were recorded. Data reflect the frequency of microtiter wells that showed visible growth. By day 5, the normal nonmutant cells appear to die off, and by days 7–10, one can easily distinguish the fast-growing mutant cells from the other specimens.

TABLE 5

Oligonucleotide Primers for the Multiplex Amplification of all Hprt Exons.

| Exon Number and Predicted Amplimer Length | SEQ ID NO: | Sense Primer | SEQ ID NO: | Antisense Primer |
|---|---|---|---|---|
| 1. 626 | 1 | TGG GAC GTC TGG TCC AAG GAT TCA | 2 | CCG AAC CCG GGA AAC TGG CCG CCC |
| 2. 572 | 3 | TGG GAT TAC ACG TGT GAA CCA ACC | 4 | GAC TCT GGC TAG AGT TCC TTC TTC |
| 3. 1059 | 5 | CCT TAT GAA ACA TGA GGG CAA AGG | 6 | TGT GAC ACA GGC AGA CTG TGG ATC |
| 4. 334 | 7 | TAG CTA GCT AAC TTC TCA AAT CTT CTA G | 8 | ATT AAC CTA GAC TGC TTC CAA GGG |
| 5. 707 | 9 | CAG GCT TCC AAA TCC CAG CAG ATG | 10 | GGG AAC CAC ATT TTG AGA ACC ACT |
| 6. 441 | 11 | GAC AGT ATT GCA GTT ATA CAT GGG G | 12 | CCA AAA TCC TCT GCC ATG CTA TTC |
| 7/8.* 1533 | 13 | GAT CGC TAG AGC CCA AGA AGT CAA G | 14 | TAT GAG GTG CTG GAA GGA GAA AAC |
| 9. 1278 | 15 | GAG GCA GAA GTC CCA TGG ATG TGT | 16 | CCG CCC AAA GGG AAC TGA TAG TC |

*Exons 7 and 8 are amplified in the same 1533 bp fragment.

We claim:

1. A method for diagnosis or prediction of an allograft rejection episode in a patient having an allograft of a solid organ or organ tissue, said method comprising the steps of:
   (a) obtaining a sample of peripheral blood of said patient;
   (b) culturing an aliquot of peripheral blood mononuclear cells from the peripheral blood sample obtained in step (a) in a medium which is selective for those cells which lack a functional hypoxanthine-guanine phosphoribosyl transferase;
   (c) culturing a second aliquot of the peripheral blood mononuclear cells from the peripheral blood sample obtained in step (a) in a medium which allows enumeration of total clonable cells;
   (d) determining a frequency of cells lacking a functional hypoxanthine-guanine
whereby a rejection episode is diagnosed or predicted when the frequency of cells lacking a functional hypoxanthine-guanine phosphoribosyl transferase is greater than 6 per 10⁶ peripheral blood mononuclear cells.

2. The method of claim 1 wherein the medium which is selective for cells lacking a functional hypoxanthine-guanine phosphoribosyl transferase comprises 6-thioguanine.

3. The method of claim 1 wherein said allograft is a cardiac transplant.

4. The method of claim 1 wherein said allograft is an organ transplant selected from the group consisting of liver, lung, heart-lung, pancreas and kidney transplant.

5. The method of claim 1 wherein said peripheral blood mononuclear cells are separated from said blood sample prior to culturing steps (b) and (c).

6. The method of claim 1 wherein sequential peripheral blood samples are taken and each sample is analyzed according to steps (b), (c) and (d), and wherein a rejection episode is diagnosed or predicted when there is an increase in the frequency of cells lacking functional hypoxanthine-guanine phosphoribosyl transferase over time as reflected in the sequential samples.

7. The method of claim 6 wherein said allograft is a cardiac transplant.

8. The method of claim 6 wherein said allograft is an organ transplant selected from the group consisting of liver, lung, heart-lung, pancreas and kidney transplant.

9. The method of claim 6 wherein said peripheral blood mononuclear cells are separated from said blood sample prior to culturing steps (b) and (c).

10. A method for diagnosis or prediction of an allograft rejection episode in a patient having an allograft of a solid organ or tissue, said method comprising the steps of:
    (a) obtaining a sample of peripheral blood of said patient;
    (b) extracting ribonucleic acid from an aliquot of peripheral blood mononuclear cells from the peripheral blood sample obtained in step (a);
    (c) performing multiplex polymerase chain reaction using oligonucleotide primers having nucleotide sequences as given in SEQ ID NOs:1–16 to amplify each of eight exons of a messenger ribonucleic acid (mRNA) encoding hypoxanthineguanine phosphoribosyl transferase on the ribonucleic acid of step (b);
    (d) analyzing the products of the multiplex polymerase chain reaction of step (c) to determine the relative abundances of the amplification products corresponding to each of the eight exons of the mRNA,
    (e) determining a frequency of cells lacking functional hypoxanthine-guanine phosphoribosyl transferase by a relative decrease in the abundance of the amplification product of one or more exons in comparison to the results obtained in carrying out steps (a) through (d) for peripheral blood mononuclear obtained from a normal individual who did not have an allograft, and
    (f) correlating the frequency of cells lacking functional hypoxanthine-guanine phosphoribosyl transferase in the sample to results obtained from a normal individual, whereby an allograft rejection episode is diagnosed or predicted when there is a greater frequency of cells lacking functional hypoxanthine-guanine phosphoribosyl transferase in the sample than in the normal individual.

11. The method of claim 10 wherein said allograft is a cardiac transplant.

12. The method of claim 10 wherein said allograft is an organ transplant selected from the group consisting of liver, lung, heart-lung, pancreas and kidney transplant.

13. The method of claim 10 wherein said peripheral blood mononuclear cells are separated from said blood sample prior to the step of extracting ribonucleic acid.

14. The method of claim 10 wherein sequential peripheral blood samples are taken and each sample is analyzed according to steps (b), (c) and. (d), and wherein a rejection episode is diagnosed or predicted when there is an increase in the frequency of cells lacking functional hypoxanthine-guanine phosphoribosyl transferase over time as reflected in the sequential samples.

* * * * *

UNITED STATES PATENT AND TRADEMARK OFFICE
CERTIFICATE OF CORRECTION

PATENT NO. : 5,635,365

DATED : June 3, 1997

INVENTOR(S) : Ansari et al.

It is certified that error appears in the above-identified patent and that said Letters Patent is hereby corrected as shown below:

On title page, item [56]

<u>In the References Cited</u>

Please add the following four publications
Gmelig-Meyling, F. (1992) *J. of Experimental Medicine* 175:297-300
Herskowitz, A. (1995) *J. of Heart Lung Transplantation* S46 #46
Ansari, A. (1995) *Circulation* 92(4):862-874
Gibbs, R. (1990) *Genomics* 7:235-244

Column 1, line 17, insert, --(PBMCs)--between "cells" and "lacking".

In Column 2, Lines 6-7, please delete "hypoxanthineguanine" and replace with --hypoxanthine-guanine--.

In Column 2, Line 46, please delete "analysis" and replace with --analyses--.

In Column 3, Line 47, please delete "of" and replace with --for--.

In Column 4, Line 52, please delete "population" and replace with --cells--.

In Column 5, Line 6, please delete "Data" and replace with --The data--.

In Column 8, Line 22, please delete "21:210-217" and replace with --31:210-217--.

In Column 9, Line 21, please delete "for only" and replace with --only for--.

In Column 9, Line 40, please add --in-- between "mutations" and ",".

In Column 9, Line 66, please delete "response" and replace with --responses--.

In Column 14, Line 28, please delete "Shedecor" and replace with --Snedecor--.

In Column 14, Lines 41-42, please delete "Wilcoxoh's" and replace with --Wilcoxon's--.

At column 15, in the heading of Table 1A, line 1, please delete "PBM" and replace with --PBMCs--.

In Claim 1(d), Column 17, Line 52, please add --phosphoribosyl transferase-- after "hypoxanthine-guanine".

In Claim 10(c), Column 18, Line 45, please delete "hypoxanthineguanine" and replace with --hypoxanthine-guanine--.

UNITED STATES PATENT AND TRADEMARK OFFICE
CERTIFICATE OF CORRECTION

PATENT NO. : 5,635,365

DATED : June 3, 1997

INVENTOR(S) : Ansari et al.

It is certified that error appears in the above-identified patent and that said Letters Patent is hereby corrected as shown below:

In Claim 10(e), Column 18, Line 56, please add --cells-- between "mononuclear" and "obtained".

Signed and Sealed this

Twenty-first Day of April, 1998

Attest:

BRUCE LEHMAN

*Attesting Officer*      *Commissioner of Patents and Trademarks*